US012569569B2

(12) United States Patent (10) Patent No.: US 12,569,569 B2
Popovtzer et al. (45) Date of Patent: Mar. 10, 2026

(54) NANO-DELIVERY SYSTEM AND THERAPEUTIC AND DIAGNOSTIC USE THEREOF

(71) Applicant: NANOCARRY THERAPEUTICS LTD., Ness Ziona (IL)

(72) Inventors: Rachela Popovtzer, Givat Shmuel (IL); Oshra Betzer, Elkana (IL); Menachem Motiei, Ashdod (IL)

(73) Assignee: NANOCARRY THERAPETICS LTD., Ness Ziona (IL)

( * ) Notice: Subject to any disclaimer, the term of this patent is extended or adjusted under 35 U.S.C. 154(b) by 593 days.

(21) Appl. No.: 17/906,204

(22) PCT Filed: Mar. 15, 2021

(86) PCT No.: PCT/IL2021/050279
§ 371 (c)(1),
(2) Date: Sep. 13, 2022

(87) PCT Pub. No.: WO2021/186430
PCT Pub. Date: Sep. 23, 2021

(65) Prior Publication Data
US 2023/0120902 A1 Apr. 20, 2023

Related U.S. Application Data

(60) Provisional application No. 62/989,752, filed on Mar. 15, 2020.

(51) Int. Cl.
| | |
|---|---|
| *A61K 47/69* | (2017.01) |
| *A61K 47/60* | (2017.01) |
| *A61K 47/64* | (2017.01) |
| *A61K 47/68* | (2017.01) |

(52) U.S. Cl.
CPC .......... *A61K 47/6929* (2017.08); *A61K 47/60* (2017.08); *A61K 47/64* (2017.08); *A61K 47/6849* (2017.08); *A61K 47/6923* (2017.08)

(58) Field of Classification Search
CPC ............ A61K 47/6929; A61K 47/6923; A61K 47/64; A61K 47/60; A61K 47/6849
See application file for complete search history.

(56) References Cited

U.S. PATENT DOCUMENTS

| | | | |
|---|---|---|---|
| 4,666,828 | A | 5/1987 | Gusella |
| 4,683,202 | A | 7/1987 | Mullis |
| 4,801,531 | A | 1/1989 | Frossard |
| 5,192,659 | A | 3/1993 | Simons |
| 5,272,057 | A | 12/1993 | Smulson |
| 9,333,163 | B2 | 5/2016 | Farokhzad |
| 9,649,391 | B2 | 5/2017 | Farokhzad |
| 10,182,986 | B2 | 1/2019 | Wiley |
| 10,363,309 | B2 | 7/2019 | Basilion et al. |
| 10,421,785 | B2 | 9/2019 | Yadid |

| | | | |
|---|---|---|---|
| 2014/0348754 | A1 | 11/2014 | Wiley et al. |
| 2017/0088585 | A1 | 3/2017 | Rahimipour |
| 2018/0015172 | A1 | 1/2018 | Muzyczka |
| 2019/0381188 | A1 | 12/2019 | Davis et al. |

FOREIGN PATENT DOCUMENTS

| | | |
|---|---|---|
| CN | 102552105 A | 7/2012 |
| WO | 2012009406 A2 | 1/2012 |
| WO | 2013034726 A1 | 3/2013 |
| WO | 2014125256 A1 | 8/2014 |
| WO | 2015101586 A1 | 7/2015 |
| WO | 2015109264 A1 | 7/2015 |
| WO | 2016081835 A2 | 5/2016 |
| WO | 2017017063 A2 | 2/2017 |
| WO | 2021130022 A1 | 7/2021 |
| WO | 2021186430 A1 | 9/2021 |
| WO | 2023286060 A1 | 1/2023 |
| WO | 2023223307 A1 | 11/2023 |

OTHER PUBLICATIONS

Betzer et al., (2017) The effect of nanoparticle size on the ability to cross the blood-brain barrier: an in vivo study. Epub ahead of print. Published in final edited form as: Nanomedicine (Lond) 12(13): 1533-1546.
Betzer et al., (2019) Insulin-coated gold nanoparticles as an effective approach for bypassing the blood-brain barrier. Proc SPIE 10891, Nanoscale Imaging, Sensing, and Actuation for Biomedical Applications XVI, 108911H (Mar. 5, 2019); https://doi.org/10.1117/ 12.2510353. 11 pages.
Brockhoff et al., (2007) Differential impact of Cetuximab, Pertuzumab and Trastuzumab on BT474 and SK-BR-3 breast cancer cell proliferation. Cell Prolif 40(4): 488-507.
Cabezón et al., (2015) Trafficking of Gold Nanoparticles Coated with the 8D3 Anti-Transferrin Receptor Antibody at the Mouse Blood-Brain Barrier. Mol Pharm 12(11): 4137-4145.
Chen et al., (2014) Polymersomes conjugated with des-octanoyl ghrelin and folate as a BBB-penetrating cancer cell-targeting delivery system. Biomaterials 35(13): 4066-4081.
Dixit et al., (2015) Dual Receptor-Targeted Theranostic Nanoparticles for Localized Delivery and Activation of Photodynamic Therapy Drug in Glioblastomas. Mol Pharm. Author manuscript; available in PMC Sep. 8, 2016. Published in final edited form as: Mol Pharm 12(9): 3250-3260.

(Continued)

*Primary Examiner* — Shirley V Gembeh
(74) *Attorney, Agent, or Firm* — RAPHAEL BELLUM PLLC

(57) ABSTRACT

The present invention provides a generic platform for delivering molecules with low blood-brain barrier (BBB) penetration into the brain. The nano-delivery system is based on a core nanoparticle which is conjugated through a first polymeric linker to a brain-internalizing transporter moiety, and is further conjugated to a second polymeric linker bound to an active agent selected from a biologically active molecule or a labeling molecule. Further provided is a process for preparation of the nano-delivery system. The present invention further provides pharmaceutical compositions comprising the nano-delivery system and its use in therapeutic and/or diagnostic methods.

16 Claims, 12 Drawing Sheets

(56)     References Cited

OTHER PUBLICATIONS

Dixit et al., (2015) Transferrin receptor-targeted theranostic gold nanoparticles for photosensitizer delivery in brain tumors. Nanoscale 7(5): 1782-1790.

Gao (2017) Perspectives on Dual Targeting Delivery Systems for Brain Tumors. Published online: Jun. 8, 2016; DOI 10.1007/s11481-016-9687-4. Published in final edited version as: J Neuroimmune Pharmacol 12(1): 6-16.

Gao et al., (2014) Study and evaluation of mechanisms of dual targeting drug delivery system with tumor microenvironment assays compared with normal assays. Acta Biomater 10(2): 858-867.

Johnsen et al., (2018) Antibody affinity and valency impact brain uptake of transferrin receptor-targeted gold nanoparticles. Theranostics 8(12): 3416-3436.

Johnsen et al., (2019) Modulating the antibody density changes the uptake and transport at the blood-brain barrier of both transferrin receptor-targeted gold nanoparticles and liposomal cargo. J Control Release 295: 237-249.

Kontermann (2012) Dual targeting strategies with bispecific antibodies. MAbs 4(2): 182-197.

Li et al., (2014) Multifunctional liposomes loaded with paclitaxel and artemether for treatment of invasive brain glioma. Biomaterials 35(21): 5591-5604.

Lippmann et al., (2014) A retinoic acid-enhanced, multicellular human blood-brain barrier model derived from stem cell sources. Sci Rep 4: 4160.

Michaelis et al., (2006) Covalent linkage of apolipoprotein e to albumin nanoparticles strongly enhances drug transport into the brain. J Pharmacol Exp Ther 317(3): 1246-1253.

Qian et al., (2008) In vivo tumor targeting and spectroscopic detection with surface-enhanced Raman nanoparticle lags. Nat Biotechnol 26(1): 83-90.

Rastinehad et al., (2019) Gold nanoshell-localized photothermal ablation of prostate tumors in a clinical pilot device study. Proc Natl Acad Sci U S A 116(37): 18590-18596.

Ruan et al., (2015) Tumor microenvironment sensitive doxorubicin delivery and release to glioma using angiopep-2 decorated gold nanoparticles. Biomaterials 37: 425-435.

Scheuer et al., (2009) Strongly enhanced antitumor activity of trastuzumab and pertuzumab combination treatment on HER2-positive human xenograft tumor models. Cancer Res 69(24): 9330-9336.

Sharma et al., (2019) Advances in nanocarriers enabled brain targeted drug delivery across blood brain barrier. Int J Pharm 559: 360-372.

Shilo et al., (2014) Transport of nanoparticles through the blood-brain barrier for imaging and therapeutic applications. Nanoscale 6(4): 2146-2152.

Stalmans et al., (2015) Cell-Penetrating Peptides Selectively Cross the Blood-Brain Barrier In Vivo. PLoS One 10(10): e0139652.

Vatine et al., (2017) Modeling Psychomotor Retardation using iPSCs from MCT8-Deficient Patients Indicates a Prominent Role for the Blood-Brain Barrier. Cell Stem Cell 20(6): 831-843.

Wiley et al., (2013) Transcytosis and brain uptake of transferrin-containing nanoparticles by tuning avidity to transferrin receptor. Proc Natl Acad Sci U S A 110(21): 8662-8667.

Xie et al., (2012) Investigation of glucose-modified liposomes using polyethylene glycols with different chain lengths as the linkers for brain targeting. Int J Nanomedicine 7: 163-175.

Zhang et al., (2019) Multitargeted Nanoparticles Deliver Synergistic Drugs across the Blood-Brain Barrier to Brain Metastases of Triple Negative Breast Cancer Cells and Tumor-Associated Macrophages. Adv Healthc Mater 8(18): e1900543.

Zou et al., (2013) Cell-penetrating Peptide-mediated therapeutic molecule delivery into the central nervous system. Curr Neuropharmacol 11(2): 197-208.

Ribovski et al. (2021), "Polymeric Nanoparticles Properties and Brain Delivery", Pharmaceutics, 13, 2045, 1-26.

Goddard et al. (2020), "Active targeting of gold nanoparticles as cancer therapeutics", Chemical Society Reviews, 49 (23), 8774-8789.

Figure 4C
Figure 4B
Figure 4A

NANO-DELIVERY SYSTEM AND THERAPEUTIC AND DIAGNOSTIC USE THEREOF

FIELD OF INVENTION

The present invention is in the field of brain-targeted nano-delivery systems for therapeutic and diagnostic uses.

BACKGROUND OF THE INVENTION

A critical problem in the treatment of neurodegenerative disorders and diseases is the difficulty in overcoming the blood-brain barrier (BBB) to deliver important therapeutic and diagnostic agents to the brain. The BBB is a highly selective semipermeable border that separates circulating blood from the central nervous system (CNS). The BBB functions mainly as a protective barrier for the brain, preventing transition of various elements, including hormones, neurotransmitters or neurotoxins, from the bloodstream into the CNS. Although specific and selective transporters located on the BBB supply the CNS with glucose, free fatty acids, amino acids, vitamins, minerals, and electrolytes, nearly all high molecular weight drugs and more than 98% of low molecular weight drugs are unable to cross the BBB.

Various nanomaterial-based drug delivery systems are being developed for overcoming the limitations associated with the BBB.

U.S. Pat. No. 10,182,986 is directed to methods of delivering a nanoparticle across the blood brain barrier to the brain of a subject by administering to the subject a nanoparticle having a nanoparticle core and a targeting agent.

Ruan, Shaobo, et al. (*Biomaterials* 37 (2015): 425-435) provides a gold nanoparticle-based delivery system, which was loaded with doxorubicin (DOX) through hydrazone, an acid-responsive linker, and functionalized with angiopep-2, a specific ligand of low density lipoprotein receptor-related protein-1 (LRP1), which could mediate the system to penetrate blood brain barrier and target to glioma cells.

Shilo, Malka, et al. (*Nanoscale* 6.4 (2014): 2146-2152) is directed to transport of insulin-targeted gold nanoparticles (INS-GNPs) through the blood-brain barrier for imaging and therapeutic applications.

There remains an unmet need for efficient systems for transporting therapeutic and/or diagnostic agents across the BBB and delivering them into the brain. A generic platform capable of delivering a wide variety of agents into the brain is highly desirable.

SUMMARY OF THE INVENTION

The present invention provides a generic platform for delivering molecules with low blood-brain barrier (BBB) penetration into the brain. The delivery system is based on a core nanoparticle which is conjugated through a first polymeric linker to a brain-internalizing transporter moiety, and is further conjugated to a second polymeric linker capable of binding a therapeutic or diagnostic agent of interest. Thus, the delivery system of the invention can be useful for the treatment and/or diagnosis of a wide range of brain-related diseases or disorders.

The inventors of the present invention have shown that various types of molecules with a poor BBB penetration, including antibodies, peptides and small molecules, were able to efficiently penetrate into mice brain while being conjugated to the delivery system of the invention, wherein the core nanoparticles were gold nanoparticles (GNPs) or iron oxide nanoparticles and the brain-internalizing transporter moiety was insulin or transferrin. The present invention is based in part on the surprising finding that the relative lengths of the first and the second polymeric linkers have a critical impact on the penetration of the delivery system through the BBB. In particular, it was unexpectedly discovered that efficient BBB penetration of GNPs conjugated to insulin and to an antibody was achieved when differently sized polymeric linkers were used for conjugating the insulin and the antibody to the core nanoparticle. It was further surprisingly found that the relative amount of the linker, which was used for conjugating the antibody affected penetration efficiency of the delivery system into the brain.

One of the beneficial features of the delivery system of the present invention is that activity of the therapeutic agent, which is conjugated to the delivery system, remains intact, such that it does not have to be detached from the nanoparticle after penetration through the BBB, e.g., by using a cleavable linker. In particular, it has been unexpectedly found that an antibody that was bound to the nano-delivery system of the invention retained its activity and functionality despite being conjugated by a stable, non-cleavable covalent linkage.

According to one aspect, there is provided a nano-delivery system comprising an inorganic nanoparticle bound to a first linear polymeric linker and to a second linear polymeric linker, wherein the first and the second linear polymeric linkers have substantially different lengths; a brain internalizing transporter moiety conjugated to the first linear polymeric linker; and an active agent selected from a biologically active molecule or a labeling molecule, wherein the agent is conjugated to the second linear polymeric linker.

According to some embodiments, the first and the second polymeric linkers are non-cleavable under physiological conditions.

According to some embodiments, the first and the second linear polymeric linkers have a difference in their respective molecular weights of at least about 1400 Da. According to further embodiments, the molecular weight of the first and the second linear polymeric linkers is within the range of 1,000-10,000 Da. In certain embodiments, the molecular weight of the first linear polymeric linker is higher than the molecular weight of the second linear polymeric linker.

According to some embodiments, the first linear polymeric linker is composed of repeating monomer units and the second linear polymeric linker is composed of the same repeating monomer units as the first linear polymeric linker, and the first linear polymeric linker has a different number of repeating monomer units than the second linear polymeric linker.

According to some embodiments, the brain-internalizing transporter moiety is covalently conjugated to the first linear polymeric linker through a first functional end group of said linker, and the active agent is covalently conjugated to the second linear polymeric linker through a second functional end group of said linker. In further embodiments, the first functional end group and the second functional end group are same.

According to certain embodiments, the inorganic nanoparticle is bound to the second linear polymeric linker through a sulfide bond and the active agent is conjugated to the second linear polymeric linker through an amide bond.

According to some embodiments, the first linear polymeric linker constitutes from about 5% mol to 60% mol of the total polymeric linkers bound to the inorganic nanoparticle.

According to some embodiments, the active agent is a biologically active molecule. The active agent can be selected from the group consisting of a macromolecule, a peptide, a small molecule, an oligonucleotide, an antisense RNA, and any combination thereof. In certain embodiments, the macromolecule is an antibody. In further embodiments, the first linear polymeric linker constitutes from about 10% mol to 40% mol of the total polymeric linkers bound to the inorganic nanoparticle.

According to some embodiments, the second linear polymeric linker constitutes from about 5% mol to 60% mol of the total polymeric linkers bound to the inorganic nanoparticle.

According to some embodiments, the first linear polymeric linker and the second linear polymeric linker independently comprise a polymer selected from the group consisting of: a polyether, a polyacrylate, a polyanhydride, a polyvinyl alcohol, a polysaccharide, a poly(N-vinylpyrrolidone), a polyglycerol (PG), a poly(N-(2-hydroxypropyl) methacrylamide), a polyoxazoline, a poly(amino acid)-based hybrid, a recombinant polypeptide, derivatives, and combinations thereof. According to certain embodiments, at least one of the first linear polymeric linker and the second linear polymeric linker is a polyether. In some exemplary embodiments, the polyether is polyethylene glycol (PEG). The polyethylene glycol can be selected from a thiolated PEG acid (HS-PEG-COOH) and a thiolated PEG amine (HS-PEG-NH2), wherein a thiolated end is bound to the inorganic nanoparticle and an acid or amine end is conjugated to the brain-internalizing transporter moiety or to the active agent.

According to some embodiments, the nano-delivery system further comprises a third polymeric linker bound to the inorganic nanoparticle, wherein the third polymeric linker is monofunctional. According to some embodiments, the third polymeric linker comprises a polymer selected from the group consisting of a polyether, a polyacrylate, a polyanhydride, a polyvinyl alcohol, a polysaccharide, a poly(N-vinylpyrrolidone), a polyglycerol (PG), a poly(N-(2-hydroxypropyl) methacrylamide), a polyoxazoline, a poly(amino acid)-based hybrid, a recombinant polypeptide, derivatives, and combinations thereof. In some exemplary embodiments, the third polymeric linker comprises a polyether, wherein the polyether is methoxy polyethylene glycol (mPEG).

According to some embodiments, the inorganic nanoparticle is selected from the group consisting of a metal nanoparticle, a metal oxide nanoparticle, a ceramic nanoparticle, and any combination thereof. The metal can be selected from the group consisting of gold, silver, platinum, iron, and any combination thereof. The metal oxide can be selected from the group consisting of iron oxide, magnesium oxide, nickel oxide, cobalt oxide, aluminum oxide, zinc oxide, copper oxide, manganese oxide, and any combination thereof. In some exemplary embodiments, the inorganic nanoparticle is selected from the group consisting of gold, iron(III) oxide, and iron(II,III) oxide. According to some embodiments, the inorganic nanoparticle has a diameter of 10-160 nm.

According to some embodiments, the brain-internalizing transporter moiety is selected from the group consisting of: insulin, an antibody specific for the insulin receptor, transferrin, an antibody specific for the transferrin receptor, a polypeptide that specifically binds to the transferrin receptor, a polypeptide that specifically binds to the insulin receptor, insulin-like growth factor 1, an antibody specific for the insulin-like growth factor receptor 1, a polypeptide that specifically binds to the insulin-like growth factor receptor 1, apolipoprotein A1, B, or E, lactoferrin, angiopep-2, a low-density lipoprotein, an antibody specific for low density lipoprotein receptor or lipoprotein receptor-related protein, a polypeptide that specifically binds to low density lipoprotein receptor or lipoprotein receptor-related protein, an antibody specific for diphtheria toxin receptor, a polypeptide that specifically binds to diphtheria toxin receptor, a BBB-penetrant cell-penetrating peptide (CPP), and any combination thereof. In certain embodiments, the brain-internalizing transporter moiety is insulin.

According to some exemplary embodiments, the inorganic nanoparticle is a gold nanoparticle, the first linear polymeric linker is a thiolated PEG5000 acid or thiolated PEG5000 amine, the second linear polymeric linker is a thiolated PEG3500 acid or thiolated PEG3500 amine, and the brain-internalizing transporter moiety is insulin.

According to some exemplary embodiments, the inorganic nanoparticle is an iron oxide nanoparticle, the first linear polymeric linker is a thiolated PEG5000 acid or thiolated PEG5000 amine, the second linear polymeric linker is a thiolated PEG3500 acid or thiolated PEG3500 amine, and the brain-internalizing transporter moiety is insulin.

According to some exemplary embodiments, the inorganic nanoparticle is a gold nanoparticle, the first linear polymeric linker is a thiolated PEG1000 acid or thiolated PEG1000 amine, the second linear polymeric linker is a thiolated PEG5000 acid or thiolated PEG5000 amine, and the brain-internalizing transporter moiety is insulin.

According to some exemplary embodiments, the inorganic nanoparticle is a gold nanoparticle, the first linear polymeric linker is a thiolated PEG5000 acid or thiolated PEG5000 amine, the second linear polymeric linker is a thiolated PEG3500 acid or thiolated PEG3500 amine, and the brain-internalizing transporter moiety is transferrin.

In another aspect, there is provided a process for preparation of the nano-delivery system according to the various embodiments described hereinabove, the process comprising sequential steps of: (a) partially coating a surface of the inorganic nanoparticle with the first linear polymeric linker followed by conjugating said first linear polymeric linker to the brain internalizing transporter moiety; and (b) partially coating the surface of the inorganic nanoparticle with the second linear polymeric linker followed by conjugating said second linear polymeric linker to the active agent, wherein step (a) and step (b) can be performed in any order.

According to some embodiments, the first polymeric linker has a first functional end group configured to bind the brain internalizing transporter moiety, and the second polymeric linker has a second functional end group configured to bind the active agent, wherein the first functional group and the second functional group are same.

According to some embodiments, the process further comprises partially coating the surface of the inorganic nanoparticle with a third polymeric linker, wherein said polymeric linker is a monofunctional linker.

According to some embodiments, the active agent is an antibody or a peptide and step (a) is performed before step (b).

According to some embodiments, the active agent is a small molecule and step (a) is performed after step (b).

According to some embodiments, each one of the first linear polymeric linker and the second linear polymeric linker is added in an amount suitable for covering between 5% and 60% of the surface of the inorganic nanoparticle.

In yet another aspect, there is provided a pharmaceutical composition comprising the nano-delivery system according to the various embodiments presented hereinabove and a pharmaceutically acceptable carrier.

According to some embodiments, the pharmaceutical composition is formulated for at least one of an intravenous (IV) administration, an intranasal (IN) administration and intrathecal (IT) administration. According to some embodiments, the pharmaceutical composition is for use in the prevention, treatment, and/or monitoring a brain-related disease or disorder in a subject in need thereof.

In still another aspect, there is provided a method of preventing, treating and/or monitoring a brain-related disease or disorder in a subject in need thereof, the method comprising administering to the subject the pharmaceutical composition according to the various embodiments described hereinabove.

According to some embodiments, the pharmaceutical composition is administered to the subject by at least one of an intravenous (IV) administration, an intranasal (IN) administration and intrathecal (IT) administration.

According to some embodiments, the method further comprises a step of imaging a brain of the subject to thereby evaluate accumulation of the nano-delivery system in the brain of said subject. The imaging can be performed using an imaging system selected from the group consisting of computed tomography imaging (CT), X-ray imaging, magnetic resonance imaging (MRI), positron emission tomography (PET), single-photon emission computed tomography (SPECT), ultrasound (US), and any combination thereof.

In yet another aspect, there is provided a nano-delivery system comprising an inorganic nanoparticle bound to a first linear polymeric linker and to a second linear polymeric linker, wherein the first and the second linear polymeric linker have substantially different lengths; and a brain internalizing transporter moiety conjugated to the first linear polymeric linker, wherein the second polymeric linker has a free functional end group configured for conjugating an active agent selected from a biologically active molecule or a labeling molecule.

According to some embodiments, the first and the second polymeric linkers are non-cleavable under physiological conditions.

According to some embodiments, the first and the second linear polymeric linkers have a difference in their respective molecular weights of at least about 1000 Da. According to some embodiments, the first and the second linear polymeric linkers have a difference in their respective molecular weights of at least about 1400 Da. According to further embodiments, the molecular weight of the first and the second linear polymeric linkers is within the range of 1,000-10,000 Da. In certain embodiments, the molecular weight of the first linear polymeric linker is higher than the molecular weight of the second linear polymeric linker.

According to some embodiments, the first linear polymeric linker is composed of repeating monomer units and the second linear polymeric linker is composed of the same repeating monomer units as the first linear polymeric linker, and the first linear polymeric linker has a different number of repeating monomer units than the second linear polymeric linker.

According to some embodiments, the brain-internalizing transporter moiety is covalently conjugated to the first linear polymeric linker through a first functional end group of said linker. According to some embodiments, the first functional end group of the first linear polymeric linker and the functional end group of the second linear polymeric linker, which is configured for conjugating an active agent, are same.

According to some embodiments, the first linear polymeric linker constitutes from about 5% mol to 60% mol of the total polymeric linkers bound to the inorganic nanoparticle. In further embodiments, the first linear polymeric linker constitutes from about 10% mol to 40% mol of the total polymeric linkers bound to the inorganic nanoparticle. According to some embodiments, the second linear polymeric linker constitutes from about 5% mol to 60% mol of the total polymeric linkers bound to the inorganic nanoparticle.

According to some embodiments, the first linear polymeric linker and the second linear polymeric linker independently comprise a polymer selected from the group consisting of: a polyether, a polyacrylate, a polyanhydride, a polyvinyl alcohol, a polysaccharide, a poly(N-vinylpyrrolidone), a polyglycerol (PG), a poly(N-(2-hydroxypropyl) methacrylamide), a polyoxazoline, a poly(amino acid)-based hybrid, a recombinant polypeptide, derivatives, and combinations thereof. According to certain embodiments, at least one of the first linear polymeric linker and the second linear polymeric linker is a polyether. In certain embodiments, the polyether is polyethylene glycol (PEG). The polyethylene glycol can be selected from a thiolated PEG acid (HS-PEG-COOH) and a thiolated PEG amine (HS-PEG-NH2), wherein a thiolated end is bound to the inorganic nanoparticle and an acid or amine end is conjugated to the brain-internalizing transporter moiety or is configured to be conjugated to the active agent.

According to some embodiments, the nano-delivery system further comprises a third polymeric linker bound to the inorganic nanoparticle, wherein the third polymeric linker is monofunctional. According to some embodiments, the third polymeric linker comprises a polymer selected from the group consisting of a polyether, a polyacrylate, a polyanhydride, a polyvinyl alcohol, a polysaccharide, a poly(N-vinylpyrrolidone), a polyglycerol (PG), a poly(N-(2-hydroxypropyl) methacrylamide), a polyoxazoline, a poly (amino acid)-based hybrid, a recombinant polypeptide, derivatives, and combinations thereof. In some exemplary embodiments, the third polymeric linker comprises a polyether, wherein the polyether is methoxy polyethylene glycol (mPEG).

According to some embodiments, the inorganic nanoparticle is selected from the group consisting of a metal nanoparticle, a metal oxide nanoparticle, a ceramic nanoparticle, and any combination thereof. The metal can be selected from the group consisting of gold, silver, platinum, iron, and any combination thereof. The metal oxide can be selected from the group consisting of iron oxide, magnesium oxide, nickel oxide, cobalt oxide, aluminum oxide, zinc oxide, copper oxide, manganese oxide, and any combination thereof. In certain embodiments, the inorganic nanoparticle is selected from the group consisting of gold, iron(III) oxide, and iron(II,III) oxide. According to some embodiments, the inorganic nanoparticle has a diameter of 10-160 nm.

According to some embodiments, the brain-internalizing transporter moiety is selected from the group consisting of: insulin, an antibody specific for the insulin receptor, transferrin, an antibody specific for the transferrin receptor, a polypeptide that specifically binds to the transferrin receptor, a polypeptide that specifically binds to the insulin receptor, insulin-like growth factor 1, an antibody specific for the insulin-like growth factor receptor 1, a polypeptide that specifically binds to the insulin-like growth factor receptor 1, apolipoprotein A1, B, or E, lactoferrin, angiopep-2, a low-density lipoprotein, an antibody specific for low density lipoprotein receptor or lipoprotein receptor-related protein, a polypeptide that specifically binds to low density lipoprotein receptor or lipoprotein receptor-related protein, an antibody specific for diphtheria toxin receptor, a polypeptide that specifically binds to diphtheria toxin receptor, a BBB-penetrant cell-penetrating peptide (CPP) and any combination thereof. In certain embodiments, the brain-internalizing transporter moiety is insulin.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 4A-4C: Representative Micro-CT 3D volume rendering images of mice brains 5 hours after the following treatments: intravenous (IV) administration of 200 μl mPEG-GNPs (control; FIG. 4A); intravenous (IV) administration of 200 μl EGFR-Ins-GNPs (FIG. 4B); and intranasal (IN) administration of 20 μl EGFR-Ins-GNPs (FIG. 4C).

FIG. 9A: WT mice; FIG. 9B: 5×FAD mice.

DETAILED DESCRIPTION OF THE INVENTION

Figure 1:
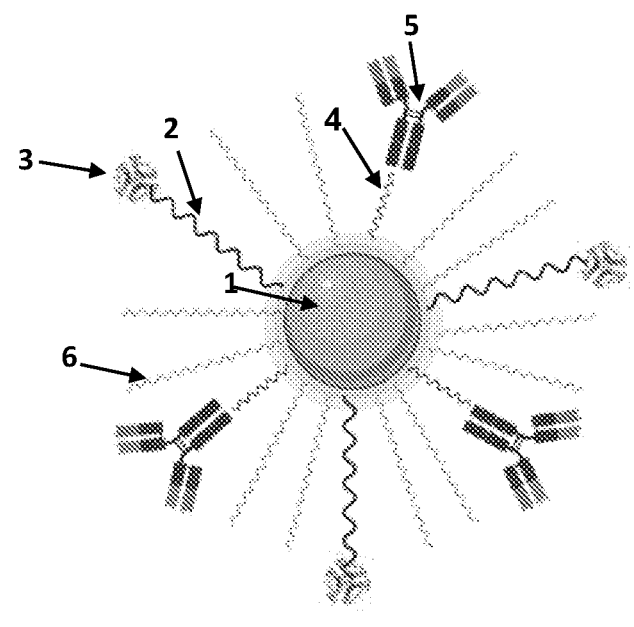
FIG. 1: Schematic illustration of a gold nanoparticle (GNP; 1) bound to: i) a first linear polymeric linker (2) which is conjugated to insulin (3); ii) a second, shorter, linear polymeric linker (4) which is conjugated to a biologically active molecule (e.g., an antibody; 5); and iii) a polymer moiety with an inert end group (6).

The present invention provides a generic nano-delivery system for delivering different types of molecules with low BBB penetration into the brain, and a process of preparation of said system. The delivery system is based on a core nanoparticle which is conjugated through a first polymeric linker to a brain-internalizing transporter moiety and is further conjugated to a second polymeric linker capable of binding a therapeutic or diagnostic agent. Without wishing to be bound by any theory or mechanism, it is hypothesized that the brain-internalizing transporter moiety promotes the penetration of the entire conjugated system through the BBB into the brain. Thus, the delivery system of the invention can be useful for the treatment and/or diagnosis of a wide range of brain-related diseases or disorders. The present invention further provides pharmaceutical compositions and methods for therapeutic and/or diagnostic use.

The invention is based, in part, on the surprising findings that nanoparticles conjugated to a brain-internalizing transporter moiety (e.g. insulin) and to a biologically active molecule can overcome the restrictive mechanisms of the blood brain barrier as well as provide a nano-delivery system for targeted delivery of diagnostic and/or therapeutic agents into the brain, without the need to release said agents from the delivery system upon the BBB penetration. As a diagnostic, this approach enables, in some embodiments, early detection of neurodegenerative diseases. As a therapeutic, in some embodiments, this approach enables the delivery of targeted therapeutic agents.

Nano-Delivery System

According to one aspect, there is provided a nano-delivery system comprising:

(a) a nanoparticle bound to a first polymeric linker and to a second polymeric linker, wherein the first and the second polymeric linkers have substantially different lengths;

(b) a brain internalizing transporter moiety conjugated to the first polymeric linker; and (c) an active agent selected from a biologically active molecule or a labeling molecule, wherein the agent is conjugated to the second polymeric linker.

According to another aspect, there is provided a nano-delivery system comprising: a nanoparticle bound to a first polymeric linker and to a second polymeric linker; and a brain internalizing transporter moiety conjugated to the first polymeric linker, wherein the first and the second polymeric linkers have substantially different lengths, and wherein the second polymeric linker has a free functional end group configured for conjugating an active agent selected from a biologically active molecule or a labeling molecule.

As used herein, the term "nano-delivery system", which may be used interchangeably with the terms "particle" or "core-shell particle", refers to a nanoparticle-based system that is capable of delivering an active agent selected from a biologically active substance or a labeling molecule, e.g., an imaging agent, to a targeted area, i.e., to a brain of a subject, or in some embodiments, to specific regions within the brain of the subject. According to the principles of the present invention, the active agent is conjugated to the external surface of a core nanoparticle through a polymeric linker, rather than being loaded or encapsulated within the nanoparticle core.

The present invention, in some embodiments, provides a particle comprising a core and a shell, wherein the core comprises a nanoparticle and the shell comprises a polymer-bound biologically active molecule or a labeling molecule and a polymer-bound brain-internalizing transporter moiety. The term 'shell,' as used herein, refers to the outer portion of the particle, with a different composition than the core. In some embodiments, the volume per volume (v/v) ratio of the brain-internalizing transporter moiety within the shell is from 5 to 60%.

As used interchangeably herein, the terms "nanoparticle" and "core nanoparticle" refer to a particle having a diameter of between 1 to 1000 nm, which constitutes the central part of the delivery system. The core nanoparticle is coated with a polymeric layer comprising at least two polymers: a first polymeric linker which is bound to a brain-internalizing transporter moiety and a second polymeric linker which has a free functional end group which is capable of binding a biologically active molecule or a labeling molecule. In some embodiments, the second polymer is bound to a biologically active molecule or a labeling molecule. The delivery system of the present invention can therefore be seen as a core-shell particle, wherein the core is the nanoparticle and the shell comprises the polymeric linkers comprising their respective conjugated molecules.

In some embodiments, the nanoparticle is selected from the group consisting of a metal nanoparticle, a metal oxide nanoparticle, a metal carbide nanoparticle, a lipid nanoparticle, a carbon-based nanoparticle, a ceramic nanoparticle, a polymeric nanoparticle and a liposome. Each possibility represents a separate embodiment of the present invention. In some embodiments, the nanoparticle is an inorganic nanoparticle. In some embodiments, the inorganic nanoparticle is selected from the group consisting of a metal nanoparticle, a metal oxide nanoparticle and a ceramic nanoparticle. In some embodiments, the inorganic nanoparticle is selected from the group consisting of a metal nanoparticle and a metal oxide nanoparticle. In some embodiments, the inorganic nanoparticle is metal nanoparticle. In other embodiments, the inorganic nanoparticle is a metal oxide nanoparticle. In specific embodiments, the inorganic nanoparticle is selected from a gold nanoparticle and an iron oxide nanoparticle.

In some embodiments, the metal nanoparticle is a magnetic nanoparticle. In some embodiments, the inorganic nanoparticle is a magnetic nanoparticle. In some embodiments, the magnetic nanoparticle is a contrast agent for magnetic resonance imaging (MRI). Any magnetic nanoparticle suitable for use as an MRI contrast agent may be used in the composition and methods of the present invention. The magnetic particle may be formed, at least in part, from any material affected by a magnetic field. Examples of suitable materials include, but are not limited to magnetite, hematite, ferrites, and materials comprising one or more of iron, cobalt, manganese, nickel, chromium, gadolinium, neodymium, dysprosium, samarium, erbium, iron carbide, iron, or a combination thereof.

In some embodiments, the inorganic nanoparticle is a contrast agent for computed tomography (CT) or X-ray imaging. In some embodiments, the inorganic nanoparticle is a metal nanoparticle which can be used as a CT or X-ray imaging contrast agent. As will be apparent to those skilled in the art, any metal and/or combination of metals suitable for use for imaging by CT or X-ray may be used in the metal nanoparticle of the present invention, in embodiments related to diagnostic use. In some embodiments, metals which can be used to form the nanoparticle of the invention are heavy metals, or metal with a high Z number. Examples of suitable metals include, but are not limited to: gold, silver, platinum, palladium, cobalt, iron, copper, tin, tantalum, vanadium, molybdenum, tungsten, osmium, iridium, rhenium, hafnium, thallium, lead, bismuth, gadolinium, dysprosium, holmium, and uranium, or a combination thereof.

According to some embodiments, the inorganic nanoparticle is a metal nanoparticle selected from the group consisting of a gold nanoparticle, a silver nanoparticle, a platinum nanoparticle, an iron nanoparticle, a copper nanoparticle, and a mixture or combination thereof. Each possibility represents a separate embodiment. In some embodiments, the metal nanoparticle is a gold (Au) nanoparticle.

In some embodiments, the inorganic nanoparticle is a metal oxide nanoparticle. In some embodiment, the metal oxide nanoparticle is selected from the group consisting of iron oxide ($Fe_2O_3$ or $Fe_3O_4$), magnesium oxide, nickel oxide, cobalt oxide, aluminum oxide, zinc oxide, copper oxide and manganese oxide, or any combination thereof. Each possibility represents a separate embodiment of the present invention. In some embodiment, the metal oxide nanoparticle comprises iron oxide selected from iron(III) oxide and iron(II,III) oxide. In some embodiments, the metal oxide nanoparticle is an iron oxide nanoparticle wherein the iron oxide is selected from iron(III) oxide and iron(II,III) oxide.

In some embodiments, the nanoparticle is selected from the group consisting of a lipid nanoparticle, a carbon-based nanoparticle, a ceramic nanoparticle, a polymeric nanoparticle and a liposome.

In some embodiments, the invention provides a plurality of particles.

According to some embodiments, the particle, i.e., the delivery system has a diameter of 5-500 nm, 6-400 nm, 8-300 nm, 10-300 nm, 10-200 nm, 10-180 nm, 10-160 nm, 10-150 nm, 10-100 nm, 20-90 nm, 20-80 nm, 20-70 nm, 20-60 nm, 25-100 nm, 25-90 nm, 25-80 nm, 25-70 nm, 25-60 nm, 25-50 nm, 30-60 nm, 40-200 nm, 40-150 nm, 40-120 nm, 40-100 nm, 40-80 nm, 40-60 nm, 50-300 nm, 50-250 nm, 50-200 nm, 50-180 nm, 50-150 nm, 60-200 nm, 70-180 nm, 80-180 nm, 90-170 nm, 100-160 nm, 100-200 nm, 150-200 nm or 150-180 nm. According to some embodiments, the particle, i.e., the delivery system has a diameter of 2-200 nm, 1-100 nm, 1-150 nm, 1-200 nm, 2-50 nm, 2-100 nm, 2-150 nm, 4-50 nm, 4-100 nm, 4-150 nm, or 4-200 nm. Each possibility represents a separate embodiment. According to some embodiments, the particle has a diameter of at least 1 nm, at least 2 nm, at least 5 nm, at least 10 nm, at least 15 nm, at least 20 nm, at least 25 nm, at least 30 nm, at least 35 nm, at least 40 nm, at least 45 nm, at least 50 nm, at least 55 nm, at least 60 nm, at least 70 nm, at least 80 nm, at least 90 nm, at least 100 nm, at least 110 nm, at least 120 nm, at least 130 nm, at least 140 nm, at least 150 nm, at least 160 nm, at least 180 nm, or at least 200 nm Each possibility represents a separate embodiment. According to some embodiments, the particle has a diameter of at most 5 nm, at most 20 nm, at most 30 nm, at most 40 nm, at most 50 nm, at most 60 nm, at most 70 nm, at most 80 nm, at most 90 nm, at most 100 nm, at most 110 nm, at most 120 nm, at most 130 nm, at most 140 nm, at most 150 nm, at most 180 nm, at most 200 nm, at most 250 nm, at most 300 nm, at most 350 nm, at most 400 nm, at most 450 nm or at most 500 nm Each possibility represents a separate embodiment.

According to some embodiments, the core nanoparticle has a diameter of 1-200 nm, 1-180 nm, 1-160 nm, 1-140 nm, 1-120 nm, 1-100 nm, 1-90 nm, 1-80 nm, 1-70 nm, 1-60 nm, 1-50 nm, 1-40 nm, 2-100 nm, 2-60 nm, 2-50 nm, 2-40 nm, 2-30 nm, 2-20 nm, 2-10 nm, 3-100 nm, 3-60 nm, 3-50 nm, 3-40 nm, 3-30 nm, 3-20 nm, 4-100 nm, 4-60 nm, 4-50 nm, 4-40 nm, 5-200 nm, 6-190 nm, 7-180 nm, 8-170 nm, 10-160 nm, 20-160 nm, 10-150 nm, 10-140 nm, 10-120 nm, 10-110 nm, 10-100 nm, 10-90 nm, 10-80 nm, 12-70 nm, 14-60 nm, 15-50 nm, 15-40 nm, 15-30 nm, 20-30 nm, 15-30 nm, 20-90 nm, 20-80 nm, 20-70 nm, 20-60 m, 20-50 nm, 20-40 nm, 20-30 nm, 30-70 nm, 30-60 nm, 40-60 nm, 10-200 nm, 20-200 nm, 30-200 nm, 40-200 nm, 50-200 nm, 60-200 nm, 70-200 nm, 80-200 nm 90-200 nm, 100-200 nm, 110-190 nm, 120-170 nm, 130-160 nm, 100-160 nm, 80-160 nm, 60-160 nm, 40-160 nm, 20-160 nm, 10-160 nm, 20-150 nm or 30-150 nm. Each possibility represents a separate embodiment. According to some embodiments, the nanoparticle has a diameter of at least 1 nm, at least 2 nm, at least 3 nm, at least 4 nm, at least 5 nm, at least 10 nm, at least 12 nm, at least 15 nm, at least 18 nm, at least 20 nm, at least 25 nm, at least 30 nm, at least 35 nm, at least 40 nm, at least 45 nm, at least 50 nm, at least 60 nm, at least 70 nm, at least 80 nm, at least 90 nm, at least 100 nm, at least 110 nm, at least 120 nm, at least 130 nm, at least 140 nm or at least 150 nm. Each possibility represents a separate embodiment. According to some embodiments, the nanoparticle has a diameter of at most 5 nm, at most 10 nm, at most 15 nm, at most 20 nm, at most 30 nm, at most 40 nm, at most 50 nm, at most 60 nm, at most 70 nm, at most 80 nm, at most 90 nm, at most 100 nm, at most 120 nm, at most 140 nm, at most 160 nm, at most 180 nm or at most 200 nm Each possibility represents a separate embodiment.

As used herein, the term "diameter" of a particle/nanoparticle can be used interchangeably with the term "size" of a particle/nanoparticle and refers to the largest linear distance between two points on the surface of a described particle/nanoparticle. The term "diameter", as used herein, encompasses sizes of spherical particles as well as of non-spherical particles, and may refer to the actual size of the particle or to its hydrodynamic diameter that includes contributions from the solvation sphere. Any method known in the art can be used to determine the size of the particle, for example transmission electron microscopy (TEM), scanning electron microscopy (SEM), and dynamic light scattering (DLS). The term "diameter" may refer to a mean diameter of a plurality of particles measured by any of the above-mentioned techniques.

In some embodiments, the core nanoparticle is coated with a polymeric layer comprising at least two polymer moieties bound to said core nanoparticle. In some embodiments, the at least two polymer moieties are polymeric linkers.

The term "coated" as used herein is intended to mean that a layer, e.g., a polymeric layer comprising a plurality of polymer moieties, is chemically attached to the surface of the core nanoparticle and thereby at least partly covers said core nanoparticle. A "nanoparticle coated with a polymeric layer" means that each polymer moiety in the polymeric layer is chemically attached to the nanoparticle through a functional end group, e.g., a thiol group, of said polymer moiety. The chemical attachment can be covalent, semi-covalent or non-covalent.

The term "polymer moiety" can be interchangeably used with the term "polymer" and refers to a molecule that contains two or more repeating subunits linked in a linear, branched, hyperbranched, dendritic or cyclic sequence, or any combination thereof. In some embodiments, the term "polymer moiety" refers to a molecule that contains at least 3 repeating subunits linked in a linear, branched, hyperbranched, dendritic or cyclic sequence, or any combination thereof. Examples of subunits include alkylene, arylene, heteroalkylene, amino acid, nucleic acid, saccharide, and the like. Examples of polymer moieties include but are not limited to poly (ethylene glycol) groups, poly (ethylene amine) groups, and poly (amino acid) groups. The terms "polymer moiety" and "polymer" encompass also polymeric linkers. As used herein, the term "polymeric linker" refers to a polymer moiety, which originally comprises at least one functional/reactive group that enables binding to a substance, e.g., a nanoparticle. In some embodiments, polymeric linker is a bifunctional polymer having at least two functional/reactive groups that enables binding to at least two substances thereby linking between said at least two substances. In some embodiments, polymeric linker is a monofunctional polymer having one functional/reactive group that enables binding to one substance, e.g., a nanoparticle. It should be understood that the terms "monofunctional", "bifunctional", "functional group", etc., as used herein, relate to the polymeric linker according to its original form prior to attachment to the core nanoparticle and/or to the brain internalizing transporter moiety or the active agent.

In some embodiments, at least one of the first and the second polymeric linkers is a linear polymeric linker. In some embodiments, the first polymeric linker is a linear polymeric linker. In some embodiments, the second polymeric linker is a linear polymeric linker. In some embodiments, the linear polymeric linker is a bifunctional linear polymer having two functional/reactive groups on the two ends of said linear polymer. In some embodiments, the first and the second polymeric linkers are both linear polymeric linkers. In some embodiments, the first and the second polymeric linkers are both linear bifunctional polymeric linkers having two functional/reactive groups on the two ends of said linear polymer.

As used herein, the term "linear" polymer/polymeric linker refers, in some embodiments, to a polymer/polymeric linker in which at least 80% of monomer units are connected in a linear fashion, i.e., in the form of a single-strand polymer chain. In further embodiments, the term "linear" polymer/polymeric linker refers to a polymer/polymeric linker in which at least 90% of monomer units are connected in a linear fashion. In yet further embodiments, the term "linear" polymer/polymeric linker refers to a polymer/polymeric linker in which about 100% of monomer units are connected in a linear fashion. The term "single-strand polymer chain" as used herein, refers to a polymer chain that comprises monomers connected in such a way that monomer units are joined to each other through two atoms, one on each monomer unit.

In some embodiments, the core nanoparticle is bound to a first polymer. In some embodiments, the core nanoparticle is bound to a second polymer. In some embodiments, the core nanoparticle is bound to a first and second polymer. In some embodiments, the core nanoparticle is bound to a first, second and third polymer. In some embodiments, the core nanoparticle is bound to a first polymeric linker. In some embodiments, the core nanoparticle is bound to a second polymeric linker. In some embodiments, the core nanoparticle is bound to a first and second polymeric linkers. In some embodiments, the core nanoparticle is bound to a first linear polymeric linker. In some embodiments, the core nanoparticle is bound to a second linear polymeric linker. In some embodiments, the core nanoparticle is bound to a first and second linear polymeric linkers. In some embodiments, the core nanoparticle is bound to a first and second polymeric linkers and an additional polymer moiety, wherein the additional polymer moiety is monofunctional, i.e., originally having a single functional end group configured for conjugating said polymer to the core nanoparticle. In some embodiments, the additional polymer is a monofunctional linker.

The term "bound" can be interchangeably used with the term "conjugated". In some embodiments, bound is covalently conjugated. The terms "covalent attachment", "covalently attached", "covalently linked" and "covalently bonded" are used herein interchangeably, and refer to the forming of a chemical bonding that is characterized by the sharing of pairs of electrons between atoms. For example, a covalently attached agent coating refers to an agent coating that forms chemical bonds with a functionalized surface of a substrate, as compared to attachment to the surface via other means, for example, adhesion or electrostatic interaction. It will be appreciated that agents (e.g., polymers) attached covalently to a surface can also be bonded via means in addition to covalent attachment.

In some embodiments, the polymer moieties and/or linkers are attached to the external surface of the core nanoparticle via a chemical attachment selected from the group consisting of: covalent attachment, semi-covalent attachment and non-covalent attachment. Each possibility represents a separate embodiment of the present invention. In some embodiments, the polymer moieties and/or linkers are attached to the external surface of the core nanoparticle via a semi-covalent attachment. As used herein, the term "semi-covalent attachment" refers to a coordinate bond wherein the shared pair of electrons which form the bond come from the same atom. In the present disclosure, a semi-covalent attachment may occur between a metal nanoparticle, e.g., gold nanoparticle, and thiol groups.

In some embodiments, the first polymeric linker comprises a polymer selected from the group consisting of a polyether, a polyacrylate, a polyanhydride, a polyvinyl alcohol, a polysaccharide, a poly(N-vinylpyrrolidone), a polyglycerol (PG), a poly(N-(2-hydroxypropyl) methacrylamide), a polyoxazoline, a poly(amino acid)-based hybrid, a recombinant polypeptide, derivatives, and combinations thereof. Each possibility represents a separate embodiment of the invention.

The term "derivative" as used herein refers to a compound whose core structure is the same as, or closely resembles that of, a parent compound, but which has a chemical or physical modification, such as a different or additional group, such as, but not limited to, an alkoxy group, a carboxy group, an amine group, a methoxy group and a thiol group.

In some embodiments, the first polymeric linker comprises a polyether. In some embodiments, the first polymeric linker is a polyether. In some embodiments, the polyether is polyethylene glycol (PEG) or a derivative thereof.

Where appropriate, the abbreviation (PEG) is used in combination with a numeric suffix which indicates the average molecular weight of the PEG. A form of PEG or a PEG species is a PEG or PEG derivative with a specified average molecular weight.

As used herein "PEG or derivatives thereof" refers to any compound including at least one polyethylene glycol moiety. PEGs exist in linear forms and branched forms comprising a multi-arm and/or grafted polyethylene glycols. The term "PEG derivative", as used herein, relates to PEG which is modified by alkylation of the terminal hydroxy group. In some embodiments, the terminal hydroxyl group is alkylated by a linear or branched C1-C6 alkyl. A PEG may further comprise a functional group. A PEG may be mono-, di-, or multifunctional polyethylene glycols.

Exemplary functional groups include, but are not limited to, the following: a hydroxyl, a carboxyl, a thiol, an amine, a phosphate, a phosphonate, a sulfate, a sulfite, a sulfonate, a sulfoxide, a sulfone, an amide, an ester, a ketone, an aldehyde, a cyano, an alkyne, an azide, and an alkene, or a combination thereof.

In some embodiments, the brain-internalizing transporter moiety is covalently conjugated to the first polymeric linker through a first functional end group of said linker, and the active agent is covalently conjugated to the second polymeric linker through a second functional end group of said linker. In some embodiments, the first functional end group and the second functional end group are same. In other embodiments, the first functional end group and the second functional end group are different.

In some embodiments, the first polymeric linker comprises a thiol (—SH) end group. In some embodiments, said first polymeric linker is chemically attached to the nanoparticle through said thiol (—SH) end group. In some embodiments, the first polymeric linker is conjugated to the brain internalizing moiety through an amide bond. In some embodiments, the nanoparticle is bound to the first polymeric linker through a sulfide bond and the brain internalizing transporter moiety is conjugated to said first polymeric linker through an amide bond. In some embodiments, the first polymeric linker within the nano-delivery system has a structure —S—R—CONH—, wherein R is a polymeric chain consisting of repeating monomer units. In other embodiments, the first polymeric linker within the nano-delivery system has a structure —S—R—NHCO—, wherein R is a polymeric chain consisting of repeating monomer units. In some embodiments, the first polymeric linker is selected from thiolated PEG acid (HS-PEG-COOH) and thiolated PEG amine (HS-PEG-NH2). It is to be understood that the HS and COOH/NH2 end groups refer to the polymeric linker prior to conjugation with the nanoparticle and the brain internalizing transporter moiety. In some embodiments, the thiol group is chemically attached to the core nanoparticle and the acid or amine group is covalently conjugated to the brain internalizing transporter moiety. In some embodiments, the first polymeric linker within the nano-delivery system has a structure selected from —S-PEG-C(O)— and —S-PEG-NH—.

In some embodiments, the first polymeric linker is a non-cleavable linker. In some embodiments, the first polymeric linker is non-cleavable under physiological conditions.

The term "non-cleavable" as used herein refers to a stable bond that is not acid or base sensitive, not sensitive to reducing or oxidizing agents, and not sensitive to enzymes that can be found in cells or the circulatory system. In some embodiments, the first and/or the second polymeric linker are devoid of pH sensitive hydrazones. In some embodiments, the first and/or the second polymeric linker are devoid of disulfide bonds. In some embodiments, the first and/or the second polymeric linker are devoid of ester bonds. It is to be understood that the term "polymeric linker is non-cleavable", is meant to encompass the bond between the nanoparticle and the polymeric linker; the bond between the respective polymeric linker and the active agent; and the bond between the respective polymeric linker and the brain internalizing transporter moiety, as well as any bond within the polymeric linker itself.

In some embodiments, the first polymeric linker has a molecular weight (MW) within a range selected from the group consisting of 500-10,000 Da, 600-9,500 Da, 700-9,000 Da, 800-8,500 Da, 800-6,000 Da, 800-5,000 Da, 800-4,000 Da, 800-3,000 Da, 800-2,000 Da, 900-8,000 Da, 1,000-7,000 Da, 1,500-6,500 Da, 2,000-6,000 Da, 3,000-6,000 Da, 4,000-6,000 Da, 3,400 to 7,000 Da, 2,000-3,000 Da, 2,000-5,000 Da, 2,000-7,000 Da, 2,000-10,000 Da, 3,000-3,400 Da, 3,000-5,000 Da, 3,000-7,000 Da, 3,000-10,000 Da, 5,000-7,000 Da, 5,000-10,000 Da, 7,000-10,000 Da. Each possibility represents a separate embodiment. According to some embodiments, the first polymeric linker has a MW of at least 1,000 Da, at least 1,500 Da, at least 2,000 Da, at least 2,500 Da, at least 3,000 Da, at least 3,400 Da, at least 4,000 Da, at least 5,000 Da, at least 6,000 Da, at least 7,000 Da, or at least 8,000 Da. Each possibility represents a separate embodiment. According to some embodiments, the first polymeric linker has a MW of at most 3,000 Da, at most 4,000 Da, at most 5,000 Da, at most 6,000 Da, at most 7,000 Da, or at most 10,000 Da. Each possibility represents a separate embodiment.

In some embodiments, the second polymeric linker comprises a polymer selected from the group consisting of a polyether, a polyacrylate, a polyanhydride, a polyvinyl alcohol, a polysaccharide, a poly(N-vinylpyrrolidone), a polyglycerol (PG), a poly(N-(2-hydroxypropyl) methacrylamide), a polyoxazoline, a poly(amino acid)-based hybrid, a recombinant polypeptide, derivatives and combinations thereof. Each possibility represents a separate embodiment of the invention.

In some embodiments, the second polymeric linker comprises a polyether. In some embodiments, the second polymeric linker is a polyether. In some embodiments, the polyether is polyethylene glycol (PEG) or a derivative thereof.

In some embodiments, the second polymeric linker comprises a thiol (—SH) end group. In some embodiments, said second polymeric linker is chemically attached to the nanoparticle through the thiol (—SH) end group. In some embodiments, the second polymeric linker is conjugated to the active agent through an amide bond. In some embodiments, the nanoparticle is bound to the second polymeric linker through a sulfide bond and the active agent is conjugated to said second polymeric linker through an amide bond. In some embodiments, the second polymeric linker within the nano-delivery system has a structure —S—R—CONH—, wherein R is a polymeric chain consisting of repeating monomer units. In other embodiments, the second polymeric linker within the nano-delivery system has a structure —S—R—NHCO—, wherein R is a polymeric chain consisting of repeating monomer units. In some embodiments, the second polymeric linker is selected from thiolated PEG acid (HS-PEG-COOH) and thiolated PEG amine (HS-PEG-NH$_2$). It is to be understood that the HS and COOH/NH2 end groups refer to the polymeric linker prior to conjugation with the nanoparticle and the active agent. In some embodiments, the thiol group is chemically attached to the core nanoparticle and the acid or amine group is covalently conjugated to the active agent. In some embodiments, the second polymeric linker within the nano-delivery system has a structure selected from —S-PEG-C(O)— and —S-PEG-NH—.

In some embodiments, the second polymeric linker is a non-cleavable linker. In some embodiments, the second polymeric linker is non-cleavable under physiological conditions.

In some embodiments, the second polymeric linker has a molecular weight (MW) between 2,000 to 7,000 Da. In some embodiments, the second polymeric linker has an MW within a range selected from the group consisting of 500-10,000 Da, 600-9,500 Da, 700-9,000 Da, 800-8,500 Da, 800-6,000 Da, 800-5,000 Da, 800-4,000 Da, 800-3,000 Da, 800-2,000 Da, 900-8,000 Da, 1,000-7,000 Da, 1,500-6,500 Da, 2,000-6,000 Da, 3,000-6,000 Da, 4,000-6,000 Da, 1,000-2,000 Da, 1,000-3,000 Da, 1,000-5,000 Da, 1,000-7,000 Da, 1,000-10,000 Da, 2,000-3,000 Da, 2,000-5,000 Da, 2,000-7,000 Da, 2,000-10,000 Da, 3,000-5,000 Da, 3,000-7,000 Da, 3,000-10,000 Da, 5,000-7,000 Da, 5,000-10,000 Da, and 7,000-10,000 Da. Each possibility represents a separate embodiment. According to some embodiments, the second polymeric linker has an MW of at least 1,000 Da, at least 2,000 Da, at least 3,000 Da, at least 4,000 Da, at least 5,000 Da, at least 6,000 Da, or at least 7,000 Da. Each possibility represents a separate embodiment. According to some embodiments, the second polymeric linker has an MW of at most 2,000 Da, at most 3,000 Da, at most 4,000 Da, at most 5,000 Da, at most 6,000, at most 7,000 Da or at most 10,000 Da. Each possibility represents a separate embodiment.

In some embodiments, the nano-delivery system comprises a polymer-bound biologically active molecule, wherein the polymer comprises a cleavable linker. According to some embodiments, the cleavable linker comprises a bond susceptible to cleavage by an endogenous molecule, located or expressed in the brain. In some embodiments, the cleavable linker is PEG succinimidyl succinate (PEGSS). According to some embodiments, the endogenous molecule is glutathione. According to some embodiments, the endogenous molecule is selected from the group comprising of proteases, nucleases, hydronium ions, and reducing agents. Each possibility represents a separate embodiment.

According to some embodiments, the nano-delivery system further comprises a cleaving molecule inducer. According to some embodiments, the cleaving molecule inducer is selected from the group comprising of N-acetyl-1-cysteine (NAC), glutathione monoester, γ-glutamylcysteine, γ-glutamylcysteine synthetase, glutathione synthetase. Each possibility represents a separate embodiment.

In some embodiments, the endogenous molecule is glutathione and the cleaving molecule inducer is selected from the group comprising of N-acetyl-1-cysteine (NAC), glutathione monoester, γ-glutamylcysteine, γ-glutamylcysteine synthetase, glutathione synthetase.

According to some embodiments, the first polymer and the second polymer are different polymers. In some embodiments the first polymer and the second polymer comprise the same polymer. In further embodiments, the first polymeric linker is composed of repeating monomer units and the second polymeric linker is composed of the same repeating monomer units as the first linear polymeric linker. In some related embodiments, the first linear polymeric linker has a different number of repeating monomer units than the second linear polymeric linker.

In some embodiments, the first and second polymeric linkers comprise the same polymer selected from the group consisting of a polyether, a polyacrylate, a polyanhydride, a polyvinyl alcohol, a polysaccharide, a poly(N-vinylpyrrolidone), a polyglycerol (PG), a poly(N-(2-hydroxypropyl) methacrylamide), a polyoxazoline, a poly(amino acid)-based hybrid, a recombinant polypeptide, derivatives and combinations thereof. In some embodiments, both the first and second polymeric linkers comprise PEG. In some embodiments, both the first and second polymeric linkers are PEG. In some embodiments, both the first and second polymeric linkers comprise thiolated PEG. In some embodiments, the first and second polymeric linkers comprise thiolated PEG acid (HS-PEG-COOH) or thiolated PEG amine (HS-PEG-NH2). In some embodiments, the first and second polymeric linkers are thiolated PEG acid (HS-PEG-COOH) or thiolated PEG amine (HS-PEG-NH₂). In some embodiments, the first and second polymeric linkers are both thiolated PEG acid (HS-PEG-COOH). In some embodiments, the first and second polymeric linkers are both thiolated PEG amine (HS-PEG-NH₂).

In some embodiments, the first and second polymeric linkers are linear. According to the principles of the present invention, the first and second linear polymeric linkers have substantially different lengths.

In some embodiments, the term "length" of a polymeric moiety or linker refers to the length of the polymer which depends on the number of monomers incorporated therein, the length of each monomer unit, the polymer chain structure (for example, whether the polymer is linear or branched), spatial conformation, deformation of valent (or binding angels) angles, and the degree of stretching or coiling.

The length of a polymer can be calculated as known in the art, for example as described in Introduction to Physical Polymer Science, Fourth Edition, L. H. Sperling, First published: 4 Nov. 2005, Chapter 3. Additionally, various computational modeling methods, which can be performed using, inter alia, Hyperchem, ACD/3D, MOE 2010.10, or Chem 3D software. can be used for evaluating the length of a polymer, as known in the art. Physical characterization methods, such as, for example, static light scattering, can also be used to assess the length of a coiled polymer. It is to be understood that when assessing the difference between the length of the first polymeric linker and the second polymeric linker, the same length definitions (or length measurement methods) must be used for both polymeric linkers.

The term "length" when referring to a linear polymer can refer to different length definitions. According to some embodiments, the term "length" refers to a displacement length, also termed herein "end-to-end" length, which is the distance between two ends of the polymer chain for a coiled polymer. End-to-end length can be expressed, for example, as Flory radius:

$$F = an^{3/5} \qquad \text{Equation I}$$

wherein F=Flory radius, a=monomer dimension, n=degree of polymerization,

According to some embodiments, the term "length" refers to contour length, which is the distance between two ends of the polymer chain when the polymer is stretched out. The contour length could be considered the maximum possible displacement length. Contour length (also termed herein "old contour length") can be calculated by dividing MW of the polymer by the MW of the monomer unit and multiplying by the length of the monomer unit. To account for binding angles, the contour length (also termed herein "new contour length") can be calculated by dividing MW of the polymer by the MW of the monomer unit, multiplying by the length of the monomer unit and further multiplying by cosine of the ((binding angle theta-180)/2).

As explained hereinabove, the length of a linear polymer can be estimated based on its molecular weight and chemical structure of a monomer unit. In order to evaluate the difference between the length of a first linear polymeric linker and a second polymeric linker, which comprise the same polymer (i.e., composed of the same type but a different number of monomer units), molecular weights of the two polymeric linkers can conveniently be used. Accordingly, in some embodiments, the first and second linear polymeric linkers have substantially different molecular weights. As used herein, the term "substantially different" refers to a difference of at least 5%, at least 6%, at least 7%, at least 8%, at least 9%, at least 10%, at least 12%, at least 15%, at least 18%, at least 20%, at least 25%, at least 30%, at least 35%, at least 40%, at least 45%, or at least 50%. Each possibility represents a separate embodiment of the present invention.

In some embodiments, the monomeric unit of the first polymeric linker and the monomeric unit of the second polymeric linker have a substantially similar molecular weight. As used herein, the term "substantially similar" refers to a similarity of at least 70%, at least 75%, at least 80%, at least 85%, at least 90%, at least 91%, at least 92%, at least 93%, at least 94%, or at least 95%. Each possibility represents a separate embodiment of the present invention.

In some embodiments, the first polymeric linker and the second polymeric linker comprise the similar polymer. In some embodiments, the first linear polymeric linker is composed of repeating monomer units and the second linear polymeric linker is composed of the same repeating monomer units as the first linear polymeric linker, wherein the first linear polymeric linker has a different number of repeating monomer units than the second linear polymeric linker. In some embodiments, the first polymeric linker and the second polymeric linker are similar except for the length of said first and said second polymeric linkers.

In some embodiments, the first and the second linear polymeric linkers have a difference in their respective molecular weights of at least about 100 Da, at least about 150 Da, at least about 200 Da, at least about 250 Da, at least about 300 Da, at least about 350 Da, at least about 400 Da, at least about 450 Da, at least about 500 Da, at least about 550 Da, at least about 600 Da, at least about 650 Da, at least about 700 Da, at least about 750 Da, at least about 800 Da, at least about 850 Da, at least about 900 Da, at least about 950 Da, at least about 1000 Da, at least about 1100 Da, at least about 1200 Da, at least about 1300 Da, at least about 1400 Da, or at least about 1500 Da. Each possibility represents a separate embodiment of the present invention.

In some embodiments, the difference between the lengths of first and the second linear polymeric linkers is configured to enable exposure of the brain internalizing transporter moiety on the external surface of the nano-delivery system, which faces the BBB. It is to be understood that the active agent is not enclosed within the nanoparticle core, but rather is attached to the external surface thereof, via a polymeric linker, similarly to the brain-internalizing moiety, which is also attached to the surface of the same nanoparticle core via a polymeric linker. Such core-shell structure, which can be formed by a relatively simple preparation process, however presented an unexpected obstacle—when using polymeric linkers of the same type and the same molecular weight for conjugating the brain internalizing moiety and the active agent, the BBB penetration efficiency of such delivery system was very low. Without wishing to being bound by theory or mechanism of action it is contemplated that the polymeric chains having similar lengths did not provide sufficient exposure of the brain-internalizing moiety on the external surface of the delivery system. In order to overcome this obstacle, polymeric linkers having different lengths were used for conjugating the brain internalizing moiety and the active agent. It has been surprisingly found by the inventors of the present invention that the higher molecular weight of the first polymeric linker than that of the second polymeric linker, wherein both polymeric linkers were composed of the same monomer units, allowed delivery of active agents of different structures and sizes, including antibodies, peptides and small molecules, into the brain. Without wishing to being bound by theory or mechanism of action, it is contemplated that the higher MW linker, which is the first polymeric linker, has both a larger contour distance and end-to-end distance than the second polymeric linker, therefore enabling exposure of the brain internalizing transporter moiety and/or shielding of the active agent, which affords for the penetration through the BBB. The nano-delivery system comprising a first polymeric linker which has a higher length and/or MW than the second polymeric linker therefore provides a generic BBB-permeable platform for the delivery of various biologically active molecules or labeling moieties.

Without further wishing to being bound by theory or mechanism of action, it is contemplated that the active agent, which is not enclosed or encapsulated within the nanoparticle core, remains accessible and active despite being bound to the delivery system. It has been unexpectedly found that an antibody that was conjugated to the polymeric linker bound to the nanoparticle, via stable, non-cleavable covalent bonds, retained its activity and functionality. It is even more surprising that a peptide targeting amyloid-beta plaques, that was conjugated to the polymeric linker bound to the nanoparticle retained its targeting ability within the brain despite being at least partly shielded by insulin, which was conjugated to the longer polymeric linker than the peptide. Accordingly, the specific composition of the nano-delivery system of the invention which ensures formation of a conjugated particle with a particular hierarchical structure, not only allows to deliver various types of active agents, but also does not interfere with the functionality of the active agent, such that cleavage of the linkage between the active agent and the nanoparticle after penetration through the BBB, is not necessarily required.

Accordingly, in some embodiments, the molecular weight of the first polymeric linker is higher than the molecular weight of the second polymeric linker. In some embodiments, the molecular weight of the first polymeric linker is higher than the molecular weight of the second polymeric linker provided that the molecular weight of the second polymeric linker is less than 4950 Da. In some embodiments, the molecular weight of the first polymeric linker is higher than the molecular weight of the second polymeric linker provided that the molecular weight of the second polymeric linker is less than 4900 Da. In some embodiments, the molecular weight of the first polymeric linker is higher than the molecular weight of the second polymeric linker provided that the molecular weight of the second polymeric linker is less than 4800 Da. In some embodiments, the molecular weight of the first polymeric linker is higher than the molecular weight of the second polymeric linker provided that the molecular weight of the second polymeric linker is less than 4780 Da. In some embodiments, the first polymeric linker is a PEG derivative having a molecular weight of about 5 kDa and the second polymeric linker is a PEG derivative having a molecular weight of about 3500 kDa.

In some embodiment, the first polymeric linker has a molecular weight which is higher than the molecular weight of the second polymeric linker. In some embodiments, the MW of the first and second polymeric linkers directly depend on the relative molecular weights of the biologically active molecule and the brain internalizing moiety. In some embodiments, the biologically active molecule has a higher Mw than the brain internalizing moiety and the first polymeric linker has a higher MW than the second polymeric linker.

In some embodiment, the first polymeric linker is longer than the second polymeric linker. In some embodiments, the first polymeric linker has a higher end-to-end distance than the second polymeric linker. In some embodiments, the first polymeric linker has a higher contour distance than the second polymeric linker.

In some embodiments, the first polymeric linker has a smaller MW than the second polymeric linker. In some related embodiments, the second polymeric linker has a MW of at least about 4000 Da and the difference between the Mw of the first polymeric linker and the second polymeric linker is at least about 2000 Da. In further embodiments, the second polymeric linker has a MW of at least about 4500 Da and the difference between the Mw of the first polymeric linker and the second polymeric linker is at least about 2500 Da. In yet further embodiments, the second polymeric linker has a MW of at least about 4700 Da and the difference between the Mw of the first polymeric linker and the second polymeric linker is at least about 3000 Da. Without wishing to being bound by theory or mechanism of action, it is contemplated that the significantly longer second linker allows folding of the polymer chain (or a higher degree of coiling), such that the actual distance between the biologically active molecule and the nanoparticle core is smaller than between the brain-internalizing moiety and the nanoparticle core, such that the biologically active molecule is at least partly shielded by the brain-internalizing moiety which is exposed on the surface of the delivery system during BBB penetration. In some related embodiments, the end-to-end distance of the first polymeric linker is higher than the end-to-end distance of the second polymeric linker, despite the higher MW of the second polymeric linker.

In some embodiments, the distance between the biologically active molecule and the nanoparticle core is smaller than the distance between the brain-internalizing moiety and the nanoparticle core. In some embodiments, at least one end group of the first polymeric linker is similar to at least one end group of the second polymeric linker. In some embodiments, at least one functional end group of the first polymeric linker is similar to at least one functional end group of the second polymeric linker. In some embodiments, the two end groups of the first polymeric linker are similar to the two end groups of the second polymeric linker. In some embodiments, the two functional end groups of the first polymeric linker are similar to the two functional end groups of the second polymeric linker.

In some embodiments, the nanoparticle is bound to an additional, third, polymer. In some embodiments, said polymer is a monofunctional polymeric linker. In some embodiments, the nanoparticle is coated with a polymeric layer comprising the first polymeric linker, the second polymeric linker, and additional, third, polymeric linker wherein the additional polymeric linker is monofunctional. The terms "third polymer" and "third polymeric linker" can be used interchangeably. In some embodiments, the third polymer functions as a spacer moiety. In some embodiments, the third polymeric linker is a linear polymeric linker. In some embodiments, the third polymer is selected from the group consisting of a polyether, a polyacrylate, a polyanhydride, a polyvinyl alcohol, a polysaccharide, a poly(N-vinylpyrrolidone), a polyglycerol (PG), a poly(N-(2-hydroxypropyl) methacrylamide), a polyoxazoline, a poly(amino acid)-based hybrid, a recombinant polypeptide, derivatives and combinations thereof.

As used herein, the term "monofunctional" means that the polymer before being conjugated to the nanoparticle has only one functional group configured to bind said polymer to the nanoparticle. The monofunctional polymeric linker is therefore neither conjugated nor capable of conjugating any moiety except for the nanoparticle.

In some embodiments, the third polymer comprises the same monomer units as the first and/or the second polymers. In some embodiments, the third polymer is bound to the nanoparticle through a thiol end group of said polymer. In some embodiments, the third polymer is a polyether.

In some embodiments, the polyether is methoxy polyethylene glycol (mPEG) or a derivative thereof. In some embodiments, the mPEG is thiolated (mPEG-SH) wherein said thiolated mPEG is bound to the core nanoparticle via the thiol end group.

In some embodiments, the third polymer has a MW between 1,000 to 7,000 Da. In some embodiments, the third polymer has a MW from 500-1,000 Da, 500-3,000 Da, 500-7,000 Da, 500-10,000 Da, 1,000-3,000 Da, 1,000-5,000 Da, 1,000-7,000 Da, 1,000-10,000 Da, 3,000-5,000 Da, 3,000-7,000 Da, 3,000-10,000 Da, 7,000-10,000 Da. Each possibility represents a separate embodiment. According to some embodiments, the third polymer has a MW of at least 1,000 Da, at least 2,000 Da, at least 3,000 Da, at least 4,000 Da, at least 5,000 Da, at least 6,000 Da, at least 7,000 Da, or at least 8,000 Da. Each possibility represents a separate embodiment. According to some embodiments, the third polymer has a MW of at most 1,000 Da, at most 2,000 Da, at most 3,000 Da, at most 4,000 Da, at most 5,000 Da, at most 6,000 Da, at most 7,000 Da, or at most 10,000 Da. Each possibility represents a separate embodiment.

In some embodiments, the v/v ratio of the third polymer in the shell is from 10-90%. In some embodiments, the v/v ratio of the third polymer in the shell is 10-20%, 10-50%, 10-70%, 10-90%, 20-50%, 20-70%, 20-90%, 50-70%, 50-90%, 70-90%. Each possibility represents a separate embodiment. In some embodiments, the v/v ratio of the third polymer in the shell is less than 20%, less than 40%, less than 50%, less than 70%, less than 90%. Each possibility represents a separate embodiment.

In some embodiments, the length of the third polymer is substantially similar to the length of the first polymeric linker or the second polymeric linker. In some embodiments, the length of the third polymer is substantially similar to the length of the first polymeric linker. In some embodiments, the length of the third polymer is substantially similar to the length of the second polymeric linker. In some embodiments, the length of the third polymer is substantially similar to the length of the polymeric linker (first or second) that its length is higher than the length of the other polymeric linker. In some embodiments, the molecular weight of the third polymer is substantially similar to the molecular weight of the first polymeric linker or the second polymeric linker. In some embodiments, the molecular weight of the third polymer is substantially similar to the molecular weight of the first polymeric linker. In some embodiments, the molecular weight of the third polymer is substantially similar to the molecular weight of the second polymeric linker. In some embodiments, the molecular weight of the third polymer is substantially similar to the molecular weight of the polymeric linker (first or second) having higher molecular weight than the other polymeric linker.

Without wishing to being bound by theory or mechanism of action, the efficacy of the nano-delivery system of the invention also depends on molar ratio of the different polymeric linkers, wherein said ratio defines the density of the brain internalizing transporter moiety and the active agent within the delivery system.

In some embodiments, the first polymeric linker constitutes about 5-70% mol, 5-60% mol, 8-60% mol, 10-60% mol, 10-50% mol, 10-40% mol, 10-30% mol, 10-25% mol, 10-20% mol, 15-50% mol, 15-40% mol, 15-30% mol, 15-25% mol, 15-20% mol, 2-10% mol, 2-20% mol, 2-50%, mol 2-60% mol, 2-70% mol, 5-10% mol, 5-20% mol, 5-70% mol, 10-20% mol, 10-50% mol, 10-70% mol, 30-50% mol, 30-60% mol, 30-70% mol, 50-60% mol or 50-70% mol of the total polymers bound to the nanoparticle. Each possibility represents a separate embodiment of the present invention. In some embodiments, first polymeric linker constitutes at least 2% mol, at least 4% mol, at least 5% mol, at least 6% mol, at least 8% mol, at least 10% mol, at least 12% mol, at least 15% mol, at least 18% mol, at least 20% mol, at least 25% mol, at least 30% mol, at least 35% mol, at least 40% mol, at least 50% mol, or at least 60% mol of the total polymers bound to the nanoparticle. Each possibility represents a separate embodiment.

In some embodiments, the second polymeric linker constitutes about 5-70% mol, 5-60% mol, 10-60% mol, 10-55% mol, 10-50% mol, 10-40% mol, 10-30% mol, 10-25% mol, 10-20% mol, 15-60% mol, 15-55% mol, 15-50% mol, 15-45% mol, 15-40% mol, 15-30% mol, 15-25% mol, 15-20% mol, 2-10% mol, 2-20% mol, 2-50%, mol 2-60% mol, 2-70% mol, 5-10% mol, 5-20% mol, 10-20% mol, 10-50% mol, 10-70% mol, 20-50% mol, 20-40% mol, 30-50% mol, 30-60% mol, 30-70% mol, 50-60% mol or 50-70% mol of the total polymers bound to the nanoparticle. Each possibility represents a separate embodiment of the present invention. In some embodiments, the second polymeric linker constitutes at least 2% mol, at least 4% mol, at least 5% mol, at least 6% mol, at least 8% mol, at least 10% mol, at least 12% mol, at least 15% mol, at least 18% mol, at least 20% mol, at least 25% mol, at least 30% mol, at least 35% mol, at least 40% mol, at least 50% mol, or at least 60% mol of the total polymers bound to the nanoparticle. Each possibility represents a separate embodiment.

In some embodiments, the third polymer constitutes about 5-90% mol, 5-85% mol, 5-80% mol, 10-80% mol, 20-78% mol, 25-75% mol, 30-75% mol, 40-75% mol, 50-75% mol, 60-75% mol, 60-70% mol, 60-80% mol, 5-60% mol, 10-60% mol, 10-55% mol, 10-50% mol, 10-40% mol, 15-60% mol, 15-55% mol, 15-50% mol, 15-45% mol or 15-40% mol of the total polymers bound to the nanoparticle. Each possibility represents a separate embodiment of the present invention. In some embodiments, the third polymer constitutes between 60-80% mol of the total polymers bound to the nanoparticle. In some embodiments, the third polymer constitutes between 50-80% mol of the total polymers bound to the nanoparticle. In some embodiments, the third polymer constitutes at least 2% mol, at least 4% mol, at least 5% mol, at least 6% mol, at least 8% mol, at least 10% mol, at least 12% mol, at least 15% mol, at least 18% mol, at least 20% mol, at least 25% mol, at least 30% mol, at least 35% mol, at least 40% mol, at least 45% mol, at least 50% mol, at least 55% mol, at least 60% mol, at least 65% mol, or at least 70% mol of the total polymers bound to the nanoparticle. Each possibility represents a separate embodiment.

In some embodiments, the first polymeric linker constitutes about 15 to 45% mol, the second polymeric linker constitutes about 10 to 45% mol, and the third polymer constitutes about 40 to 75% mol of the total polymers bound to the nanoparticle.

It is to be understood that the % mol of each polymer moiety is dependent on the other polymer moieties bound to the nanoparticle, such that the total % mol of the polymers does not exceed 100%.

In some embodiments, the first polymeric linker, second polymeric linker and third polymer are in a (w/w/w) ratio of at least 5:5:90 to 60:30:30.

In some embodiments, the first polymer and the second polymer are in a (w/w) ratio of at least 40:60 to 95:5.

According to the principles of the present invention, the nano-delivery system comprises a brain-internalizing transporter moiety conjugated to the first polymeric linker. The term "brain-internalizing transporter moiety", which can be used interchangeably herein with the term "brain-internalizing moiety" refers to a molecule that can specifically bind to a receptor or surface protein expressed by a cellular component of the BBB. The three major cellular elements of the brain microvasculature, which collectively form the BBB, are brain endothelial cells, astrocyte end feet and pericytes (PCs). In some embodiments, the brain-internalizing transporter moiety can bind to a receptor or surface protein expressed by a brain endothelial cell. In some embodiments, the brain-internalizing transporter moiety can bind to a receptor or surface protein expressed by astrocyte end feet. In some embodiments, the brain-internalizing transporter moiety can bind to a receptor or surface protein expressed by pericytes (PCs). Without wishing to be bound by any theory or mechanism, it is hypothesized that the brain internalizing moiety promotes the transportation of the entire nano-delivery system through the BBB, possibly through a receptor mediated transcytosis (RMT) or receptor mediated endocytosis (RME) mechanism.

In some embodiments, the brain-internalizing moiety is selected from, but not limited to, insulin, an antibody specific for the insulin receptor, transferrin, an antibody specific for the transferrin receptor, a polypeptide that specifically binds to the transferrin receptor, a polypeptide that specifically binds to the insulin receptor, insulin-like growth factor 1, an antibody specific for the insulin-like growth factor receptor 1, a polypeptide that specifically binds to the insulin-like growth factor receptor 1, apolipoprotein A1, B, or E, lactoferrin, angiopep-2, an antibody specific for low density lipoprotein receptor or lipoprotein receptor-related protein, a polypeptide that specifically binds to low density lipoprotein receptor or lipoprotein receptor-related protein, an antibody specific for diphtheria toxin receptor, a polypeptide that specifically binds to diphtheria toxin receptor, and a BBB-penetrant cell-penetrating peptide (CPP). Each possibility represents a separate embodiment of the present invention. As used herein, the term "cell-penetrating peptide (CPP)" refers to a peptide that has an enhanced ability to cross cell membrane bilayer without causing a significant lethal membrane damage. The term "BBB-penetrant CPP" refers to a cell-penetrating peptide that can cross the membrane of BBB cells and is therefore able to penetrate into the brain (Zou, Li-li, et al. *Current neuropharmacology* 11.2 (2013): 197-208, and Stalmans, Sofie, et al. *PloS one* 10.10 (2015): e0139652).

Other cellular proteins capable of facilitating transcytosis that are known in the art can also be used as a brain-internalizing moiety. In some embodiments, the brain-internalizing moiety is selected from the group consisting of insulin, transferrin, a low-density lipoprotein, apolipoprotein A1, B, or E, and lactoferrin. Each possibility represents a separate embodiment of the present invention. In some embodiments, the brain-internalizing moiety is selected from the group consisting of insulin and transferrin. In some embodiments, the brain-internalizing moiety is insulin. In some embodiments, the molecular weight (MW) of the insulin is about 5 kilodaltons (kD).

In some embodiments, a v/v ratio of the brain-internalizing moiety (e.g. insulin) within the shell is between 2-10%, 2-20%, 2-50%, 2-60%, 2-70%, 5-10%, 5-20%, 5-50%, 5-60%, 5-70%, 10-20%, 10-50%, 10-60%, 10-70%, 30-50%, 30-60%, 30-70%, 50-60%, 50-70%. In some embodiments, a v/v ratio of the insulin within the shell is between 5-60%. In some embodiments, the v/v ratio of the insulin within the shell is at least 2%, at least 5%, at least 10%, at least 30%, at least 50%, at least 60%, at least 70%. Each possibility represents a separate embodiment.

According to the principles of the present invention, the second polymeric linker is conjugated to an active agent selected from a biologically active molecule and a labeling molecule. As used herein, the term "active agent" refers to an agent that is intended to be delivered into the brain of a subject and is capable of being used as a therapeutic or diagnostic agent. According to some embodiments, the active agent is characterized by a poor BBB penetration. According to some embodiments, upon penetration through the BBB, the active agent can further target the nano-delivery system to a specific region within the brain, e.g., the hippocampus, the striatum, the cerebellum and the cortex. According to some embodiments, upon penetration through the BBB, the active agent can target the nano-delivery system to specific cell population inside the brain, e.g., glioma cells, microglial cells, and neuronal cells.

In some embodiments, the active agent is a macromolecule. The term 'macromolecule,' as defined herein refers to a very large molecule, commonly formed via polymerization of monomers. In some embodiments, the macromolecule is a protein. In some embodiments, the macromolecule is an enzyme.

In some embodiments, the macromolecule is an antibody. As used herein, the term "antibody" refers to a polypeptide or group of polypeptides that include at least one binding domain that is formed from the folding of polypeptide chains having three-dimensional binding spaces with internal surface shapes and charge distributions complementary to the features of an antigenic determinant of an antigen. An antibody typically has a tetrameric form, comprising two identical pairs of polypeptide chains, each pair having one "light" and one "heavy" chain. The variable regions of each light/heavy chain pair form an antibody binding site. An antibody may be oligoclonal, polyclonal, monoclonal, chimeric, camelised, CDR-grafted, multi-specific, bi-specific, catalytic, humanized, fully human, anti-idiotypic and antibodies that can be labeled in soluble or bound form as well as fragments, including epitope-binding fragments, variants or derivatives thereof, either alone or in combination with other amino acid sequences. An antibody may be from any species. The term antibody also includes binding fragments, including, but not limited to Fv, Fab, Fab', F(ab')2 single stranded antibody (svFC), dimeric variable region (Diabody) and disulphide-linked variable region (dsFv). In particular, antibodies include immunoglobulin molecules and immunologically active fragments of immunoglobulin molecules, i.e., molecules that contain an antigen binding site. Antibody fragments may or may not be fused to another immunoglobulin domain including but not limited to, an Fc region or fragment thereof. The skilled artisan will further appreciate that other fusion products may be generated including but not limited to, scFv-Fc fusions, variable region (e.g., VL and VH)~ Fc fusions and scFv-scFv-Fc fusions.

In some embodiments, the active agent conjugated to the second polymeric linker is a biologically active molecule. In some embodiments, the biologically active molecule is contiguous to the second polymeric linker. The term "biologically active molecule" as used herein, refers to compounds or molecules that are capable of eliciting or modifying a biological response in a system. In some embodiments, the biologically active molecule is a therapeutic agent. In some embodiments, the biologically active molecule has therapeutic applications. In some embodiments, the biologically active molecule has diagnostic applications. In some embodiments, the biologically active molecule has both therapeutic and diagnostic applications.

In some embodiments, the biologically active molecule comprises a small molecule, a macromolecule, an oligonucleotide, an antisense RNA, a peptide or any combination thereof. In some embodiments, the biologically active molecule is selected from the group consisting of a macromolecule, a peptide and a small molecule. In some embodiments, the biologically active molecule is selected from the group consisting of an antibody, a peptide and a small molecule. Each possibility represents a separate embodiment of the present invention.

The term "peptide" as used herein refers to any polymer compound produced by amide bond formation between an .alpha.-carboxyl group of one D- or L-amino acid and an .alpha.-amino group of another D- or L-amino acid.

The term "small molecule", as used herein, refers to organic or inorganic molecules either synthesized or found in nature, generally having a molecular weight less than 1000 Da. Also encompassed by the term "small molecule" is any fragment of a peptide, protein, or antibody, including native sequences and variants falling within the molecular weight range stated above.

In some embodiments, the biologically active molecule is a therapeutic agent that is effective in treating a brain-related disease or disorder. In some embodiments, the biologically active molecule is an antibody used for the treatment or diagnosis of a brain-related disease.

As used herein, the term "brain-related disease or disorder" refers to any disease or disorder that causes malfunction of the brain or any cell thereof. Non-limiting examples of brain-related diseases and disorders are neurodegenerative disorders such as Parkinson's disease, Alzheimer's disease, Huntington's disease and Dementia; neuromuscular diseases such as amyotrophic lateral sclerosis (ALS) and motor neuron disease; neurodevelopmental diseases such as autism spectrum disorders and attention deficit hyperactivity disorder (ADHD); autoimmune brain-related diseases such as multiple sclerosis (MS); neuropsychiatric disorders such as schizophrenia, drug addiction, smoking addiction, eating disorders, obsessive-compulsive disorder, various forms of depression, anxiety disorders, cognitive disorders and affective disorders; seizure disorders such as epilepsy; pain disorders such as migraine; cerebrovascular disorders including traumatic brain injury and stroke; brain-related cancers such as brain and nerve tumors, brain metastasis, glioma, glioblastoma (GBM), and gliosarcoma (GS); neurogenetic diseases such as Huntington's disease, Kennedy's disease, metabolic disorders, lysosomal storage disorders and Duchenne; and neuroinfectious diseases.

In some embodiments, active agent is a labeling molecule. The term "labeling molecule", as used herein, refers to a molecule that is capable of producing a signal detectable by suitable detection means, such as but not limited to radioactive molecules and fluorescent molecules. In some embodiments, the labeling molecule has diagnostic applications. In some embodiments, the labeling molecule is a diagnostic agent. In some embodiments, the labeling molecule comprises a small molecule, a macromolecule, an oligonucleotide, an antisense RNA, a peptide or any combination thereof. In some embodiments, the labeling molecule is a small molecule. In some embodiments, the labeling molecule is an antibody.

In some embodiments, the active agent is an antibody having a molecular weight (MW) of 100-120 kD, 100-150 kD, 100-200 kD, 100-250 kD, 150-200 kD, 150-250 kD, 200-250 kD. Each possibility represents a separate embodiment. In some embodiments, the antibody has an MW of at least 100 kD, at least 110 kD, at least 120 kD, at least 130 kD, at least 140 kD, at least 150 kD, at least 160 kD, at least 180 kD, at least 200 kD, at least 250 kD. Each possibility represents a separate embodiment. In some embodiments, the antibody has an MW of 150-200 kD. In some embodiments, the antibody has an MW of 130-180 kD. In some embodiments, the antibody has an MW of 140-160 kD.

In some embodiments, the antibody has a MW of 150-200 kD and the second polymeric linker (PEG) has a MW of at least 2,000 Da, at least 2,500 Da or at least 3,000 Da. In some embodiments, the antibody has a MW of 150-200 kD and the second polymeric linker (PEG) has a MW of at most 2,000 Da, at most 2,500 Da, at most 3,000 Da, at most 3,500 Da, at most 4,000 Da, at most 5,000 Da or at most 6,000 Da. In some such embodiments, the brain internalizing moiety is insulin with a MW of 5-6 kD and the first polymeric linker has a MW of at least 2,000 Da, at least 2,500 Da, at least 3,000 Da, at least 3,400 Da, at least 4,000 Da or at least 4,500 Da.

In some embodiments, the v/v ratio of the antibody in the shell is between 2-10%, 2-20%, 2-30%, 2-40%, 5-10%, 5-20%, 5-30%, 5-40%, 10-20%, 10-30%, 10-40%, 20-30%, 20-40%, 30-40%. In some embodiments, a v/v ratio of the antibody in the shell is between 5-30%. In some embodiments, the v/v ratio of the antibody in the shell is at least 2%, at least 5%, at least 10%, at least 30%, at least 40%. Each possibility represents a separate embodiment.

In some embodiments, the v/v ratio of the macromolecule in the shell is between 2-10%, 2-20%, 2-30%, 2-40%, 5-10%, 5-20%, 5-30%, 5-40%, 10-20%, 10-30%, 10-40%, 20-30%, 20-40%, 30-40%. In some embodiments, a v/v ratio of the macromolecule in the shell is between 5-30%. In some embodiments, the v/v ratio of the macromolecule in the shell is at least 2%, at least 5%, at least 10%, at least 30%, at least 40%. Each possibility represents a separate embodiment.

In some embodiments, the active agent has a MW smaller than 1,000 Daltons (Da). In some embodiments, the active molecule has a MW of 10-50 Da, 10-100 Da, 10-500 Da, 10-1,000 Da, 50-100 Da, 50-500 Da, 50-1,000 Da, 100-300 Da, 100-500 Da, 100-800 Da, 100-1,000 Da, 500-800 Da, 500-1,000 Da, 800-1,000 Da. Each possibility represents a separate embodiment.

In some embodiments, the active agent has a MW less than 1,000 Da, less than 900 Da, less than 800 Da, less than 700 Da, less than 600 Da, less than 500 Da, less than 400 Da, less than 300 Da, less than 200 Da, less than 100 Da. Each possibility represents a separate embodiment. In some embodiments, the active agent has a MW more than 100 Da, more than 200 Da, more than 300 Da, more than 400 Da, more than 500 Da, more than 600 Da, more than 700 Da, more than 800 Da, more than 900 Da. Each possibility represents a separate embodiment.

In some embodiments, the active agent is a small molecule. In some embodiments, the biologically active molecule is a small molecule. In some embodiments, the biologically active molecule is an oligonucleotide. In some embodiments, the biologically active molecule is antisense RNA. In some embodiments, the biologically active molecule is a peptide. In some embodiments, the biologically active molecule is a drug.

In some embodiments, the v/v ratio of the biologically active molecule within the shell is 40-95%. In some embodiments, the v/v ratio is between 30-40%, 30-50%, 30-70%, 30-90%, 30-95%, 30-98%, 40-50%, 40-70%, 40-90%, 40-95%, 40-98%, 60-70%, 60-90%, 60-95%, 60-98%, 70-90%, 70-95%, 70-98%, 80-90%, 80-95%, 80-98%. Each possibility represents a separate embodiment.

According to some embodiments, the inorganic nanoparticle is a gold nanoparticle. According to some embodiments, the first linear polymeric linker is a thiolated PEG5000 acid or thiolated PEG5000 amine. According to some embodiments, the second linear polymeric linker is a thiolated PEG3500 acid or thiolated PEG3500 amine. According to some embodiments, the brain-internalizing transporter moiety is insulin. The nano-delivery system can further include an active agent, selected from an antibody, a peptide and a small molecule.

According to some embodiments, the inorganic nanoparticle is an iron oxide nanoparticle. According to some embodiments, the first linear polymeric linker is a thiolated PEG5000 acid or thiolated PEG5000 amine. According to some embodiments, the second linear polymeric linker is a thiolated PEG3500 acid or thiolated PEG3500 amine. According to some embodiments, the brain-internalizing transporter moiety is insulin. The nano-delivery system can further include an active agent, selected from an antibody, a peptide and a small molecule.

According to some embodiments, the inorganic nanoparticle is a gold nanoparticle. According to some embodiments, the first linear polymeric linker is a thiolated PEG5000 acid or thiolated PEG5000 amine. According to some embodiments, the second linear polymeric linker is a thiolated PEG3500 acid or thiolated PEG3500 amine. According to some embodiments, the brain-internalizing transporter moiety is transferrin. The nano-delivery system can further include an active agent, selected from an antibody, a peptide and a small molecule.

According to some embodiments, the inorganic nanoparticle is a gold nanoparticle. According to some embodiments, the first linear polymeric linker is a thiolated PEG1000 acid or thiolated PEG1000 amine. According to some embodiments, the second linear polymeric linker is a thiolated PEG5000 acid or thiolated PEG5000 amine. According to some embodiments, the brain-internalizing transporter moiety is insulin. The nano-delivery system can further include an active agent, selected from an antibody, a peptide and a small molecule.

Preparation Process

According to another aspect, there is provided a process for preparation of the nano-delivery system of the invention, in all embodiments thereof as described above, the process comprising the steps of sequentially:

a) partially coating a surface of the inorganic nanoparticle with the first linear polymeric linker followed by conjugating said first linear polymeric linker to the brain internalizing transporter moiety; and b) partially coating the surface of the inorganic nanoparticle with the second linear polymeric linker followed by conjugating said second linear polymeric linker to the active agent, wherein step (a) and step (b) can be performed in any order.

The term "partially coating", as used herein, refers to conjugating a plurality of the respective polymeric linkers to the surface of a nanoparticle, such that the plurality of linkers partly covers the surface of the nanoparticle at a density level below the saturation level of the naked nanoparticle.

Any method known in the art can be used for determining the amount of polymer required for achieving full-density (i.e., 100%) coating of a nanoparticle, and accordingly the amount needed for partial coating. For example, adding different amounts of polymer to the nanoparticle solution and measuring the concentration of the free polymer in supernatants after centrifugation is a widely used method. Alternatively, any characterization method that is sensitive to changes in coating density can be used, such as zeta potential and DLS. Furthermore, theoretical calculations can be performed to determine the amount of polymer needed to achieve complete coating according to the surface area of the nanoparticle. For example, it was previously shown that a thiol-PEG molecule occupies a footprint area 0.35 nm$^2$ on gold nanoparticle surface (Qian, Ximei, et al. *Nature biotechnology* 26.1 (2008): 83-90). Accordingly, the amount of a thiol-PEG linker required to cover 100% of the surface of a gold nanoparticle can be calculated based on the mean diameter of the GNP.

In some embodiments, each one of the first linear polymeric linker and the second linear polymeric linker is added in an amount suitable for covering between 5% and 60% of the surface of the inorganic nanoparticle.

In some embodiments, step (a) comprises coating between 5%-60%, 10-60%, 10-50%, 10-40%, 10-30%, 10-25%, 10-20%, 15-50%, 15-40%, 15-30%, 15-25%, 15-20%, 2-10%, 2-20%, 2-50%, 2-60%, 2-70%, 5-10%, 5-20%, 5-70%, 10-20%, 10-50%, 10-70%, 30-50%, 30-60% mol, 30-70%, 50-60% or 50-70% of the surface of the inorganic nanoparticle.

In some embodiments, step (b) comprises coating between 5%-60%, 10-60%, 10-50%, 10-40%, 10-30%, 10-25%, 10-20%, 15-50%, 15-40%, 15-30%, 15-25%, 15-20%, 2-10%, 2-20%, 2-50%, 2-60%, 2-70%, 5-10%, 5-20%, 5-70%, 10-20%, 10-50%, 10-70%, 30-50%, 30-60% mol, 30-70%, 50-60% or 50-70% of the surface of the inorganic nanoparticle.

In some embodiments, the process further comprises partially coating the surface of the inorganic nanoparticle with a third polymeric linker, wherein said polymeric linker is a monofunctional linker.

In some embodiments, step (a) is performed before step (b). In some embodiments, the process further comprising centrifugation between step (a) and step (b). In other embodiments, step (a) is performed after step (b). In some embodiments, the process further comprising centrifugation between step (b) and step (a). In some embodiments, the active agent is an antibody or a peptide and step (a) is performed before step (b). In some embodiments, the active agent is a small molecule and step (a) is performed after step (b).

The nanoparticle, the first polymeric linker, the second polymeric linker, the brain-internalizing transporter moiety, and the active agent suitable for use in the preparation process are those described hereinabove in connection with the various aspects and embodiments of the nano-delivery system.

Pharmaceutical Compositions

In yet another aspect, there is provided a pharmaceutical composition comprising the nano-delivery system according to the various embodiments described hereinabove and a pharmaceutically acceptable carrier.

As used herein, a "pharmaceutically acceptable formulation," "pharmaceutical composition" or "pharmaceutically acceptable composition" may include any of a number of carriers such as solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (Remington's, 1990). Pharmaceutical compositions containing the presently described nanoparticles as the active ingredient can be prepared according to conventional pharmaceutical compounding techniques. See, for example, Remington's Pharmaceutical Sciences, 18th Ed., Mack Publishing Co., Easton, Pa. (1990). See also, Remington: The Science and Practice of Pharmacy, 21st Ed., Lippincott Williams & Wilkins, Philadelphia, Pa. (2005).

A composition may comprise different types of carriers depending on whether it is to be administered in solid, liquid or aerosol form, and whether it needs be sterile for such routes of administration as injection. A person of ordinary skill in the art would be familiar with techniques for generating sterile solutions for injection or application by any other route. Sterile injectable solutions are prepared by incorporating the active compounds in the required amount in an appropriate solvent with various other ingredients familiar to a person of skill in the art.

The carrier may comprise, in total, from about 0.1% to about 99.99999% by weight of the pharmaceutical compositions presented herein.

According to some embodiments, the pharmaceutical composition is formulated for systemic administration. According to some embodiments, the pharmaceutical composition is formulated for systemic administration selected from intravenous and intranasal administration. According to some embodiments, the pharmaceutical composition is formulated for intravenous administration. According to some embodiments, the pharmaceutical composition is formulated for intranasal administration. According to some embodiments, the pharmaceutical composition is formulated for intrathecal administration.

The compositions contemplated herein may take the form of solutions, suspensions, emulsions, aerosols, combinations thereof, or any other pharmaceutical acceptable composition as would commonly be known in the art.

In some embodiments, the carrier is a solvent. For a non-limiting example, the composition may be disposed in the solvent. Such a solvent includes any suitable solvent known in the art such as water, saline, phosphate-buffered saline.

The formulation of the composition may vary depending upon the route of administration. For parenteral administration in an aqueous solution, for example, the solution should be suitably buffered if necessary and the liquid diluent first rendered isotonic with sufficient saline or glucose. Sterile aqueous media which can be employed will be known to those of skill in the art in light of the present disclosure.

Supplementary active ingredients can also be incorporated into the compositions. For human administration, preparations should meet sterility and general safety and purity standards as required by FDA Office of Biologics standards. Administration may be by any known route.

In certain embodiments, a pharmaceutical composition includes at least about 0.001 g to about 1 g of the particle disclosed herein per kilogram of a subject.

The pharmaceutical composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof. The composition must be stable under the conditions of manufacture and storage, and preserved against the contaminating action of microorganisms, such as bacteria and fungi. It will be appreciated that exotoxin contamination should be kept minimally at a safe level, for example, less than 0.5 ng/mg protein.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. In many cases, it will be preferable to include isotonic agents, such as, for example, sugars, sodium chloride or combinations thereof.

In other embodiments, a nasal solutions or sprays, aerosols or inhalants may be used. Nasal solutions are usually aqueous solutions designed to be administered to the nasal passages in drops or sprays.

Solid compositions for oral administration are also contemplated. In these embodiments, the solid composition may comprise, for example, solutions, suspensions, emulsions, tablets, pills, capsules, sustained release formulations, buccal compositions, troches, elixirs, suspensions, syrups, or combinations thereof.

Sterile injectable solutions are prepared by incorporating the active compounds (e.g., nanoparticles) in the required amount in the appropriate solvent with various other ingredients enumerated above. The liquid medium should be suitably buffered if necessary and the liquid diluent first rendered isotonic prior to injection with sufficient saline or glucose.

The dose can be repeated as needed as determined by those of ordinary skill in the art. Thus, in some embodiments of the methods set forth herein, a single dose is contemplated. In other embodiments, two or more doses are contemplated. Where more than one dose is administered to a subject, the time interval between doses can be any time interval as determined by those of ordinary skill in the art.

Therapeutic and Diagnostic Use of the Composition

According to some embodiments, the pharmaceutical composition is for use in the prevention of a disease in a subject in need thereof. According to some embodiments, the pharmaceutical composition is for use in the treatment of a disease in a subject in need thereof. According to some embodiments, the pharmaceutical composition is for use in monitoring a disease in a subject in need thereof. In some embodiments, the disease is a brain-related disease or disorder.

In some embodiments, the disease is a central nervous system disease. According to some embodiments, the disorder is a brain disorder.

In some embodiments, the pharmaceutical composition is for use in the treatment of a brain-related disease or disorders. In some embodiments, the brain-related disease or disorder is selected from the group consisting of a brain-related cancer, a neurodegenerative disorder, a neuromuscular disease, a neurodevelopmental disease, an autoimmune brain-related disease, a neuropsychiatric disorder, a seizure disorder, a pain disorders, a cerebrovascular disorder, a neurogenetic disease and a neuroinfectious disease.

In some embodiments, the brain-related disease is a brain-related cancer. The term "brain related cancer" as used herein encompasses both primary brain tumors and metastatic brain tumors. In some embodiments, the brain related cancer is selected from but not limited to the group consisting of brain and nerve tumors, brain metastasis, glioma, glioblastoma (GBM), and gliosarcoma (GS). In some embodiments, the brain-related disease is a neurodegenerative disorder. In some embodiments, the neurodegenerative disorder is selected from the group consisting of Parkinson's disease, Alzheimer's disease, Huntington's disease and Dementia. In some embodiments, the brain-related disease is a neuromuscular disease. In some embodiments, the neuromuscular disease is selected from the group consisting of amyotrophic lateral sclerosis (ALS) and motor neuron disease. In some embodiments, the brain-related disease is a neurodevelopmental disease. In some embodiments, the neurodevelopmental disease is selected from the group consisting of autism spectrum disorders and attention deficit hyperactivity disorder (ADHD). In some embodiments, the brain-related disease is multiple sclerosis (MS). In some embodiments, the brain-related disease is a neuropsychiatric disorder. In some embodiments, the neuropsychiatric disorder is selected from the group consisting of schizophrenia, drug addiction, smoking addiction, eating disorders, obsessive-compulsive disorder, various forms of depression, anxiety disorders, cognitive disorders and affective disorders. In some embodiments, the brain-related disease is a seizure disorder. In some embodiments, the seizure disorder is epilepsy. In some embodiments, the brain-related disease is a pain disorder. In some embodiments, the brain-related disease is a cerebrovascular disorder. In some embodiments, the cerebrovascular disorder is selected from traumatic brain injury and stroke. In some embodiments, the brain-related disease is a neurogenetic disease. In some embodiments, the neurogenetic disease is selected from the group consisting of Huntington's disease, Kennedy's disease, metabolic disorders, lysosomal storage disorders and Duchenne. In some embodiments, the brain-related disease is a neuroinfectious disease.

In some embodiments, the brain-related disease is Alzheimer's disease. In some embodiments, the brain-related disease is Parkinson's disease. According to some embodiments, the brain-related disease is Huntington's disease, spinocerebellar ataxia, amyotrophic lateral sclerosis, Friedreich's ataxia, motor neuron disease (Lou Gehrig's disease) or spinal muscular atrophy. According to some embodiments, the brain-related disease is a prion disease.

As used herein, the term "subject" refers to any animal (e.g., a mammal), including, but not limited to, humans, non-human primates, rodents, and the like (e.g., which is to be the recipient of a particular treatment). Typically, the terms "subject" and "patient" are used interchangeably, unless indicated otherwise herein.

In some embodiments, the subject is a human subject. In some embodiments, the subject is at risk of being afflicted with a brain-related disease, a disorder, or a medical condition. In some embodiments, the subject is diagnosed with a brain-related disease, a disorder, or a medical condition. In some embodiments, the subject is diagnosed with a brain-related genetic disorder. In some embodiments, the subject is at risk of being afflicted with a neurodegenerative disease. In some embodiments, the subject is diagnosed with a neurodegenerative disease. In some embodiments, the subject is diagnosed with Alzheimer's disease. In some embodiments, the subject is diagnosed with Parkinson's disease.

As used herein, a subject at risk of being afflicted with a disease, a disorder, or a medical condition, is a subject that presents one or more signs or symptoms indicative of a disease, a disorder, or a medical condition or is being screened for a disease, a disorder, or a medical condition (e.g., during a routine physical). A subject at risk of being afflicted with a disease, a disorder, or a medical condition, may also have one or more risk factors. A subject at risk of being afflicted with a disease, a disorder, or a medical condition encompasses an individual that has not been previously tested for the disease, disorder, or medical condition. However, a subject at risk of being afflicted with a disease, a disorder, or a medical condition, also encompasses an individual who has received a preliminary diagnosis but for whom a confirmatory test (e.g., biopsy and/or histology) has not been done or for whom the stage of the disease, disorder, or medical condition is not known. The term further includes people who once had the disease, disorder, or medical condition (e.g., an individual in remission).

A subject at risk of being afflicted with a brain-related disease, disorder, or medical condition may be diagnosed as having or alternatively found not to have the brain-related disease, disorder, or medical condition.

As used herein, a subject diagnosed with brain-related disease, disorder, or medical condition, may be diagnosed using any suitable method, including but not limited to, biopsy, x-ray, blood test, and the diagnostic methods of the present invention. A "preliminary diagnosis" is one based only on visual (e.g., CT scan or the presence of a lump) and antigen tests.

In some embodiments, the subject is afflicted with a brain-related disease, disorder, or medical condition, and the imaging method is used for determining the stage of the disease, disorder, or medical condition. In some embodiments, the subject afflicted with a brain-related disease, disorder, or medical condition, was treated with a drug, and the imaging method is used for follow-up of the treatment.

As used herein, the terms "treatment", "treating", or "ameliorating" of a disease, disorder, or condition, refer to alleviation of at least one symptom thereof, a reduction in the severity thereof, or inhibition of the progression thereof. Treatment need not mean that the disease, disorder, or condition is totally cured. To be an effective treatment, a useful composition herein needs only to reduce the severity of a disease, disorder, or condition, reduce the severity of symptoms associated therewith, or provide improvement to a patient or subject's quality of life.

In some embodiments, the present invention provides a method of administering an active agent t for the prevention, treatment and/or monitoring a brain-related disease in a subject in need thereof, the method comprising administering to the subject the pharmaceutical composition comprising the nano-delivery system of the invention in all embodiments thereof. According to some currently preferred embodiments, the method comprises delivering the active agent to a brain region of the subject.

In some embodiments, the method further comprises a step of imaging the brain region of the subject to thereby evaluate accumulation of the nano-delivery system in the brain of said subject. In some embodiments, the imaging is performed using an imaging system selected from the group consisting of: computed tomography imaging (CT), X-ray imaging, magnetic resonance imaging (MRI), positron emission tomography (PET), single-photon emission computed tomography (SPECT), ultrasound (US), and any combination thereof.

In some embodiments, the present invention provides a theranostic method. The method comprises the steps of administering to a subject in need thereof the pharmaceutical composition of the invention and imaging a target site of the subject to determine whether the nanoparticles accumulated in the target site of the subject. In some embodiments, the target site is a site in the brain of the subject.

In some embodiments, administering the composition to the subject can be done by using any method known to those of ordinary skill in the art. The mode of administering may vary based on the application. For example, the mode of administration may vary depending on the particular cell, brain region, or subject to be imaged. For example, administering the composition may be done intravenously, intracerebrally, intracranially, intrathecally, intracerebroventricular, into the substantia nigra or the region of the substantia nigra, intradermally, intraarterially, intraperitoneally, intralesionally, intratracheally, intranasally, intramuscularly, intraperitoneally, subcutaneously, orally, topically, locally, by inhalation (e.g., aerosol inhalation), by injection, by infusion, by subarachnoid infusion, by transmucosal infusion, by intracarotid infusion, by continuous infusion, by localized perfusion bathing target cells directly, via a catheter, via a lavage, or by other method or any combination of the forgoing as would be known to one of ordinary skill in the art.

In some embodiments, the pharmaceutical composition is administered to the subject by a systemic administration route. In some embodiments, the systemic administration is selected from an intravenous (IV) administration and an intranasal (IN) administration. In some embodiments, the pharmaceutical composition is administered to the subject by intrathecal (IT) administration.

In some embodiments, the particle is administered intravenously. In some embodiments, the particle is administered intranasally.

Upon formulation, compositions will be administered in a manner compatible with the dosage formulation and in such amount as is effective. For example, the nanoparticles may be administered in such an amount that is effective for a particular imaging application desired.

An effective amount of the pharmaceutical composition is determined based on the intended goal, for example, based on the imaging method and the subject or portion of a subject to be imaged. The quantity to be administered may also vary based on the particular route of administration to be used. The composition is preferably administered in a "safe and effective amount." As used herein, the term "safe and effective amount" refers to the quantity of a composition which is sufficient for the intended goal (e.g., imaging) without undue adverse side effects (such as toxicity, irritation, or allergic response).

In some embodiments, imaging of the target site is performed by an imaging technique that utilizes penetrating radiation. According to some embodiments, the imaging technique is selected from the group comprising of magnetic resonance imaging (MRI), computed tomography imaging (CT), X-ray imaging, positron emission tomography (PET), single-photon emission computed tomography (SPECT), and ultrasound (US).

In some embodiments, the imaging step is performed 0.5 to 96 hours post the administering step. In some embodiments, the imaging step is performed 0.5 to 48 hours post the administering step. In some embodiments, the imaging step is performed 0.5 to 24 hours post the administering step. In some embodiments, the imaging step is performed 0.5 to 12 hours post the administering step. In some embodiments, the imaging step is performed 1 to 12 hours post the administering step. In some embodiments, the imaging step is performed 1 to 6 hours post the administering step. In some embodiments, the imaging step is performed within 96 hours from the administering step. In some embodiments, the imaging step is performed within 48 hours from the administering step. In some embodiments, the imaging step is performed within 24 hours from the administering step. In some embodiments, the imaging step is performed within 12 hours from the administering step. In some embodiments, the imaging step is performed within 6 hours from the administering step.

In some embodiments, the method comprises the step of determining whether the nanoparticles accumulated in the target site of the subject. In some embodiments, treatment decision may be not to administer a therapy. In some embodiments, the analysis of the imaging data is used for deciding on a route of treatment adequate to the patient. In some embodiments, deciding on a route of treatment adequate to the patient depends, for example, on the stage of the disease, disorder, or medical condition, as well as on the health state of the patient. In some embodiments, the route of treatment includes one or more protocols of treatment selected from the group comprising of: intravenous, intranasal, intraperitoneal, intramuscular and subcutaneous and any other biological or inorganic product intended for treatment. In some embodiments, a treatment is administered subsequent to the imaging. In some embodiments, a treatment is administered to the subject in real time, while imaging the subject.

In some embodiments, imaging and treating the subject are performed simultaneously. In some embodiments, the biologically active molecule may be activated in the subject target site subsequent to imaging.

Kits

In some embodiments, the invention provides kits comprising one or more compositions disclosed herein. In some embodiments, the invention provides kits useful for methods disclosed herein. For example, a kit may include a container having a sterile reservoir that houses any composition disclosed herein. In some embodiments, the kit further includes instructions. For example, a kit may include the instructions for administering the composition to a subject (e.g., indication, dosage, methods etc.). In yet another example the kit may include instructions of to apply the compositions and methods of the invention to imaging systems e.g., computed tomography (CT), ultrasound (US), magnetic resonance imaging (MRI).

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Any concentration ranges, percentage range, or ratio range recited herein are to be understood to include concentrations, percentages or ratios of any integer within that range and fractions thereof, such as one tenth and one hundredth of an integer, unless otherwise indicated.

Any number range recited herein relating to any physical feature, such as polymer subunits, size or thickness, are to be understood to include any integer within the recited range, unless otherwise indicated.

As used herein, the term "about" when combined with a value refers to plus and minus 10% of the reference value. For example, a molecular weight of about 1000 Da refers to a molecular weight of 1000 Da+−100 Da.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The term "plurality" means "two or more", unless expressly specified otherwise.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Various embodiments and aspects of the present invention as delineated hereinabove and as claimed in the claims section below find experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Strategies for Protein Purification and Characterization—A Laboratory Course Manual" CSHL Press (1996); all of which are incorporated by reference. Other general references are provided throughout this document.

Example 1: Preparation and Characterization of Gold Nanoparticles (GNPs) Coated with Insulin and an EGFR Antibody (EGFR & Ins-GNPs)

FIG. 1 shows a schematic illustration of a non-limiting example particle, showing a gold nanoparticle (GNP) coated with a polymeric layer comprising a first polymeric linker (e.g., —S-PEG-C(O)—, ~5 kDa) which is conjugated to insulin; a second polymeric linker (e.g., —S-PEG-C(O)—, ~3.5 kDa) which is conjugated to a biologically active molecule (e.g., an antibody); and a third, monofunctional polymer moiety (e.g., —S-PEG-O—CH$_3$~5 kDa).

GNP Synthesis 20 nm spherical GNPs were prepared by citrate reduction of HAuCl$_4$. A total of 414 µl of 50% w/v of HAuCl$_4$ solution in 200 ml distilled water was boiled in an oil bath on a heating plate while being stirred. After boiling, 4.04 ml of a 10% sodium citrate solution were added and the mixture was stirred while boiling for another 10 minutes. The solution was removed from the plate and after cooling to room temperature, the solution was centrifuged until precipitation of the nanoparticles.
Conjugation of PEG5000 & Insulin to the GNPs GNPs were first partially coated (85% of particle surface) with mPEG-SH (~5 kDa; 70% of particle surface) and a heterofunctional HS-PEG-COOH (~5 kDa; 15% of particle surface). The amount of mPEG-SH and HS-PEG-COOH required for the partial coating was derived from theoretical calculations based on the finding that thiol-PEG molecule occupies a footprint area 0.35 nm$^2$ on gold nanoparticle surface (Qian, Ximei, et al. Nature biotechnology 26.1 (2008): 83-90). Conjugation was performed by adding a mixture of HS-PEG-COOH (145 µl, 50 mg/ml) and mPEG-SH (677 µl, 50 mg/ml) to the GNP solution and mixing for two hours. The solution was then ultra-centrifuged at 15,000 RPM for 20 minutes and then again at 20,000 RPM for 15 minutes. The precipitate, containing the PEG-coated GNPs (total 85% coating) was transferred to a vial. Insulin was then covalently conjugated to the carboxylic group of the HS-PEG-COOH by addition of excess amount of insulin on ice together with EDC (1-ethyl-3-(3-dimethylaminopropyl) carbodiimide HCl) and NHS (N-hydroxysulfosuccinimide sodium salt) followed by mixing for two hours. Then, the solution was centrifuged at 14,000 RPM for 30 minutes (maintained at a cool temperature) and the lower phase, containing the Ins-PEG-GNPs was transferred into a vial.
Conjugation of PEG3500 & EGFR Ab to the GNPs In order to further conjugate an EGFR Ab to the GNPs, 102 µl of HS-PEG-COOH (~3.5 kDa) solution (50 mg/ml) were added to the partially coated GNPs to coat the remaining 15% of particle surface. The solution was then mixed for two hours at 4° C. followed by centrifugation at 14,000 RPM for 30 minutes. EGFR Ab was then covalently conjugated to the free carboxylic groups of the HS-PEG-COOH (~3.5 kDa) by addition of excess amount of EGFR Ab together with EDC and NHS. The solution was then stirred for 2 hours at 4° C. followed by centrifugation until a final concentration of 30 mg/ml Au was reached.

Figure 2:
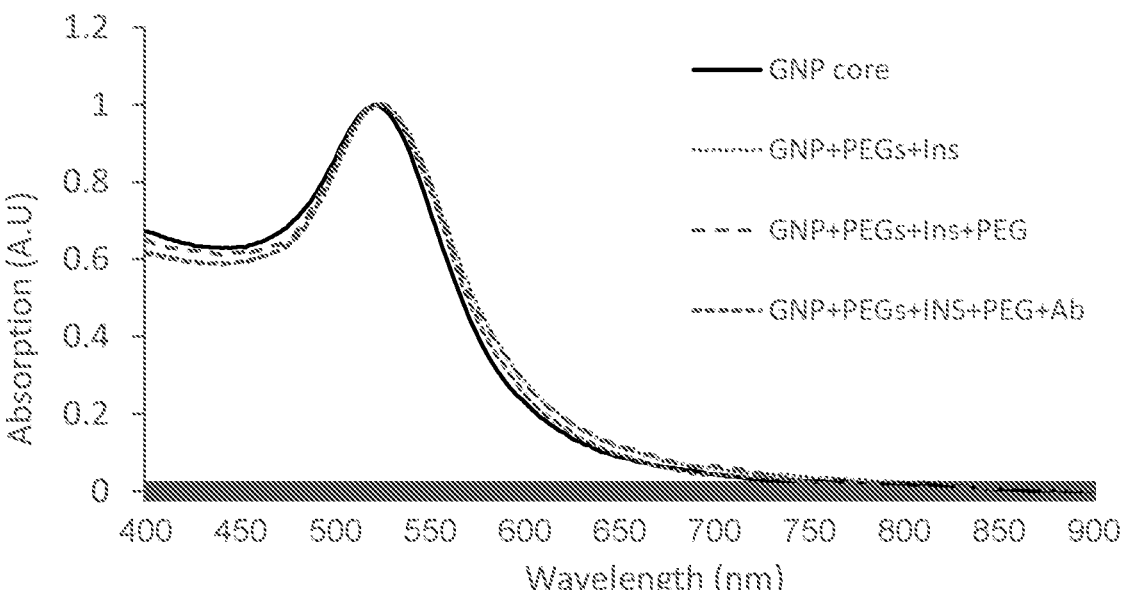
FIG. 2: Ultraviolet-visible spectroscopy of EGFR & Ins-GNPs after various synthesis steps: before coating (GNPs); after coating with PEGs (~5 kDa) and insulin (GNPs+PEGs+Ins); after coating with additional PEG linker (~3.5 kDa; GNPs+PEGs+Ins+PEG); and finally after conjugation of EGFR Ab (GNPs+PEGs+Ins+PEG+Ab).

The EGFR & Ins-GNPs were characterized following each step of preparation using ultraviolet-visible spectroscopy (FIG. 2). The shift of the UV-Vis signal following the different coating levels confirmed a sacksful coating.

Figure 3:
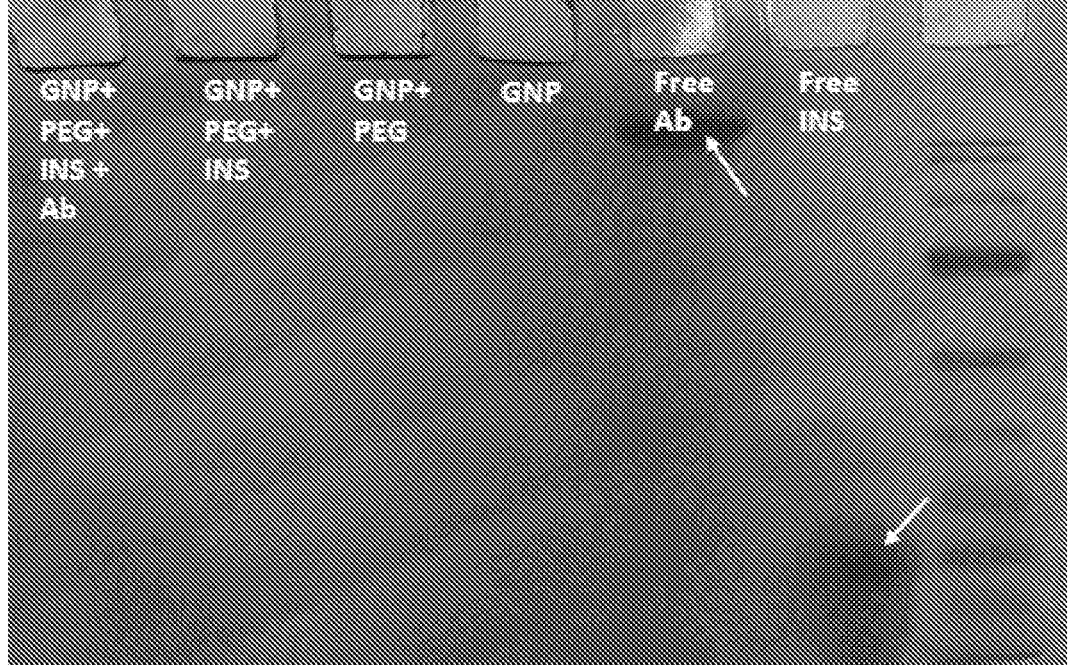
FIG. 3: SDS-PAGE of free insulin (free INS), free EGFR Ab (free Ab), GNP, PEG-coated GNP (GNP+PEG), Insulin-coated GNP (GNP+PEG+INS) and EGFR+Ins-GNP (GNP+PEG+INS+Ab).

The covalent conjugation between the PEG linkers and the insulin and EGFR Ab was confirmed by Sodium dodecyl sulfate-polyacrylamide gel electrophoresis (SDS-PAGE) assay. Free insulin, free EGFR Ab, GNP, PEG-coated GNP (GNP+PEG), Insulin-coated GNP (GNP+PEG+INS) and EGFR & Ins-GNP (GNP+PEG+INS+Ab) were analyzed by SDS-PAGE (run at 120V, 60 min). As can be seen in FIG. 3, neither insulin nor EGFR Ab were separated from the GNPs during the electrophoresis process, indicating a stable covalent conjugation.

Example 2: Delivery of EGFR & Ins-GNPs into Mice Brain

13 Male BALB/c mice, each weighing 20-25 g, were divided into three groups. Mice in the first group (control; n=3) were administered IV with control GNPs (200 µl; 30 mg/ml). The control GNPs were prepared by coating 20 nm spherical GNPs with a layer of 5 kDa mPEG-SH (mPEG-GNPs). Mice in the second group (n=5) were administered intravenously into the tail vein with 200 µl of 30 mg/ml EGFR-Ins-GNPs. Mice in the third group (n=5) were administered intranasally with 20 µl EGFR-Ins-GNPs. All mice were anesthetized and sacrificed 5 hours post-administration. The mice underwent perfusion to remove all the particles residing within the blood vessels.

After sacrifice, mice brains were scanned by a micro-CT scanner. As can be seen in FIG. 4A, no GNP accumulation was observed in the brains of control mice who received untargeted mPEG-GNPs. In contrast, micro-CT images of mice brains from the second and third groups (FIGS. 4B and 4C, respectively) show a clearly visible EGFR & Ins-GNP accumulation.

GNPs accumulation in mice brains was further quantitatively measured by ICP-MS analysis of mice brains samples, showing at total amount of 13.45 µg Au in the brain following intravenous administration (approximately 1.6646E+14 particles according to theoretical calculations) and 0.42 µg Au in the brain following intranasal administration (approximately 5.19772E+12 particles according to theoretical calculations).

Overall, the results indicate that the insulin ligand facilitates transportation of the GNP complex through the BBB, resulting in a remarkable penetration of EGFR & Ins-GNP into the brain after either intravenous or intranasal administration, with a higher amount of particles penetrated into the brain by IV administration. However, the micro-CT images showed that the particles reach different locations when administered through the IV or IN route. Thus, the results further suggest that the EGFR & Ins-GNPs can serve as CT contrast agents for labeling specific brain regions in which they accumulate.

Example 3: Biodistribution and Pharmacokinetic Profile of EGFR & Ins-GNPs

In order to examine the quantity of EGFR & Ins-GNPs in the brain, as well as the whole body biodistribution, EGFR & Ins-GNPs were intravenously injected into the tail vein of male BALB/c mice. Mice were sacrificed at various time points until one month post injection (n=3 for each time point) and the brain, kidney and liver of the mice were taken for ICP-MS analysis to quantify the amount of gold in the organs over time.

Figure 5A:
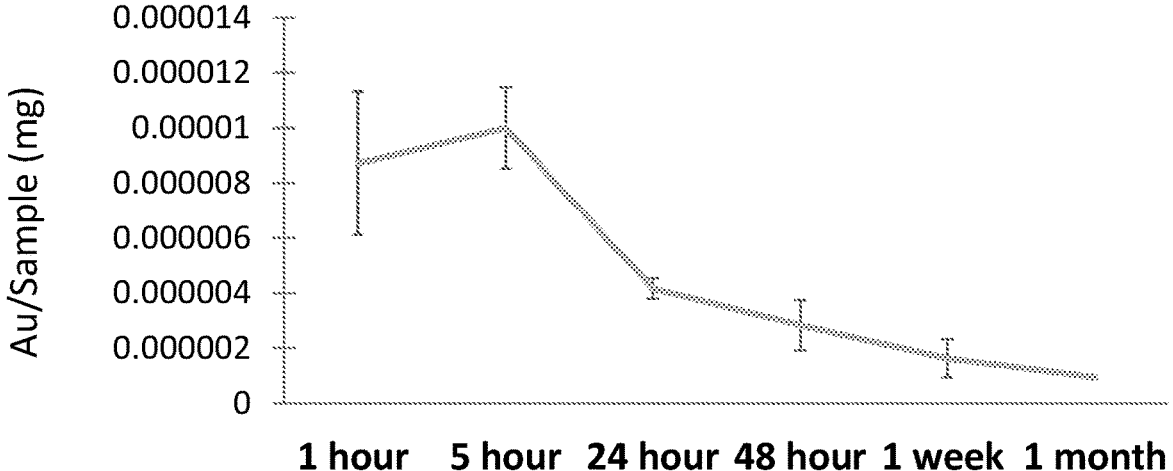
FIG. 5A: Quantification of the amount of Au (mg) found in brain tissue of mice at various time point after intravenous administration of EGFR & Ins-GNPs, as measured by ICP-MS analysis.

As demonstrated in FIG. 5A, the EGFR & Ins-GNPs rapidly accumulated within the brain and remained at high concentration until 5 hours post injection. Then, gradual clearance of the particles from the brain was observed with a negligible amount of gold at 1 week post injection and full clearance at 1 month post injection.

Figure 5B:
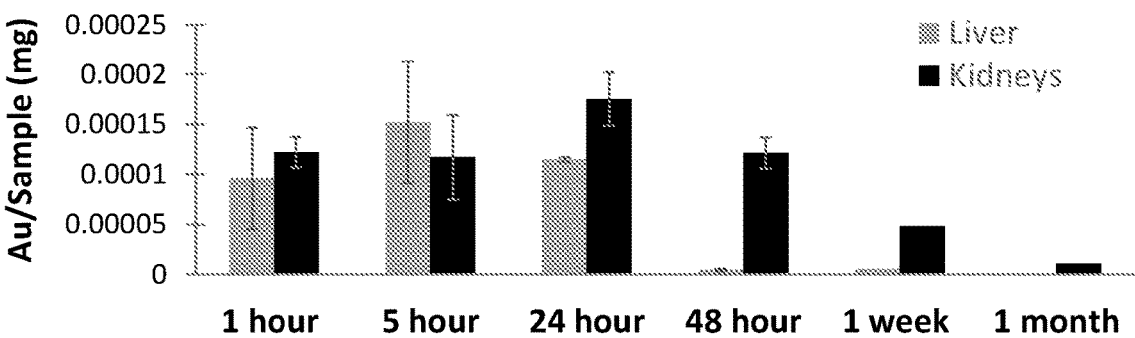
FIG. 5B: Quantification of the amount of Au (mg) found in the kidney and liver of mice at various time point after intravenous administration of EGFR & Ins-GNPs, as measured by ICP-MS analysis.

In addition, as can be seen in FIG. 5B, the EGFR & Ins-GNPs accumulated in the kidney and liver until 24 hours post injection, and then cleared from these organs until 1 month post injection.

Example 4: Delivery of IgG1 & Ins-GNPs into Mice Brain

GNPs coated with a fluorescent antibody IgG1 (Mouse Monoclonal IgG1 Alexa Fluor 488 Isotype, clone 11711) and insulin (IgG1 & Ins-GNPs) were synthesized as described in Example 1, with the following differences:

1) Fluorescent IgG1 antibody was used instead of EGFR Ab.
2) HS-PEG-COOH (~5 kDa): 193 µl were added instead of 145 µl (~20% of particle surface).
3) mPEG-SH (~5 kDa): 580 µl were added instead of 677 µl (~60% of particle surface).
4) HS-PEG-COOH (~3.5 kDa): 136 µl were added instead of 102 µl (~20% of particle surface).

Mice were injected IV either with 200 µl of 30 mg/ml IgG1 & Ins-GNPs (n=5) or with equivalent amount (0.4 mg) of free fluorescent IgG1 antibody (n=3). Eight hours post injection, mice brains were extracted and analyzed using ICP-MS (n=3) or immunocytochemistry (n=2).

Figure 6A:
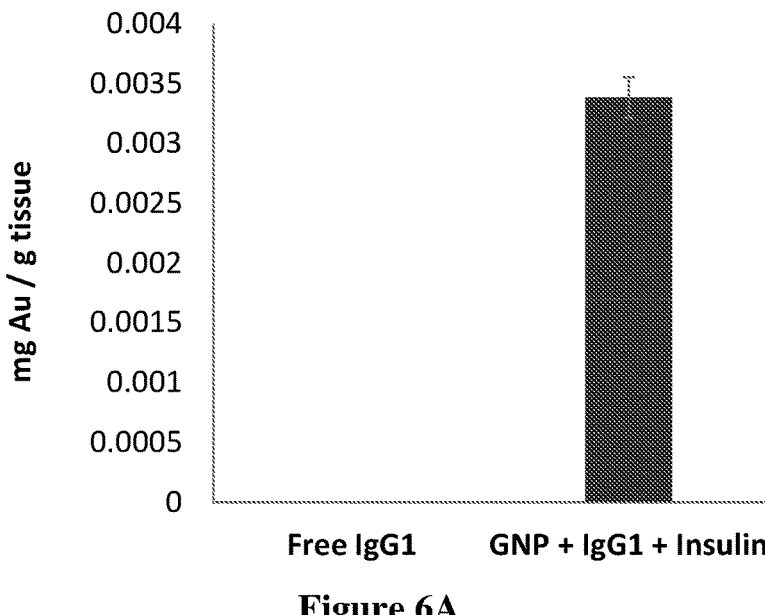
FIG. 6A: Quantification of the amount of Au found in brain tissue of mice at 8 hours after intravenous administration of IgG1 & Ins-GNPs or free fluorescent IgG1 antibody, as measured by ICP-MS analysis (mg Au per gr tissue).

As demonstrated in FIG. 6A, quantitative ICP-MS analysis indicated successful penetration of IgG1 & Ins-GNPs into the brain (FIG. 6A).

Figure 6B:
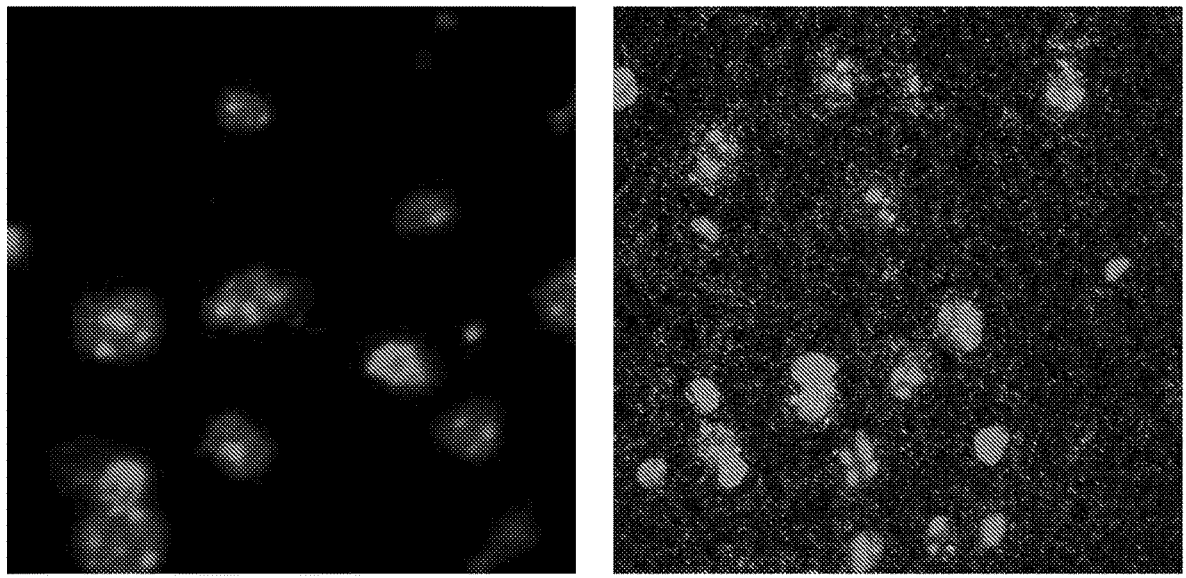
FIG. 6B: Representative confocal immunocytochemistry fluorescence images of brain sections of mice treated with IgG1 & Ins-GNPs (right panel) or with free fluorescent antibody (left panel).

For immunocytochemistry fluorescence (IHC F), Fixation and Permeabilization method (FPM) used was FPM13, and sections were taken from the cerebral cortex region. 7 um Brain Frozen section were prepared using Cryostat, and immuno-stained. 4',6-diamidino-2-phenylindole (DAPI) was used for nuclear DNA labeling. Fluorescence antibodies signals were detected and photos were taken using confocal microscope. All photos were taken in the same exposure conditions. As can be seen in FIG. 6B, high fluorescence was observed in brain sections of mice treated with IgG1 & Ins-GNPs (right panel) while no fluorescence, except for DAPI signal, was seen in brain sections of mice treated with free fluorescent antibody (left panel). The results indicate that the targeted GNP system facilitates the brain penetration of antibodies which natively have a limited ability to transport across the BBB.

Example 5: Delivery of Anti-Iba1 & Ins-GNPs into Mice Brain

GNPs coated with insulin and anti-Iba1 fluorescent antibody (an antibody for microglial cells) were synthesized as described in Example 4, using fluorescent anti-Iba1 (Rabbit Monoclonal—Alexa fluor 647) instead of IgG1 Ab.

Mice were injected IV either with 200 µl of 30 mg/ml Anti-Iba1 & Ins-GNPs or with equivalent amount (0.1 mg) of free fluorescent anti-Iba1. 7 hours post injection, mice were sacrificed and underwent perfusión. Then, mice brains were sectioned and imaged using a super resolution microscopy. The vascular muscles were stained with Alexa Fluor 568 and the BBB endothelium cells were stained with CD31—Alexa Fluor 488.

Figure 7A:
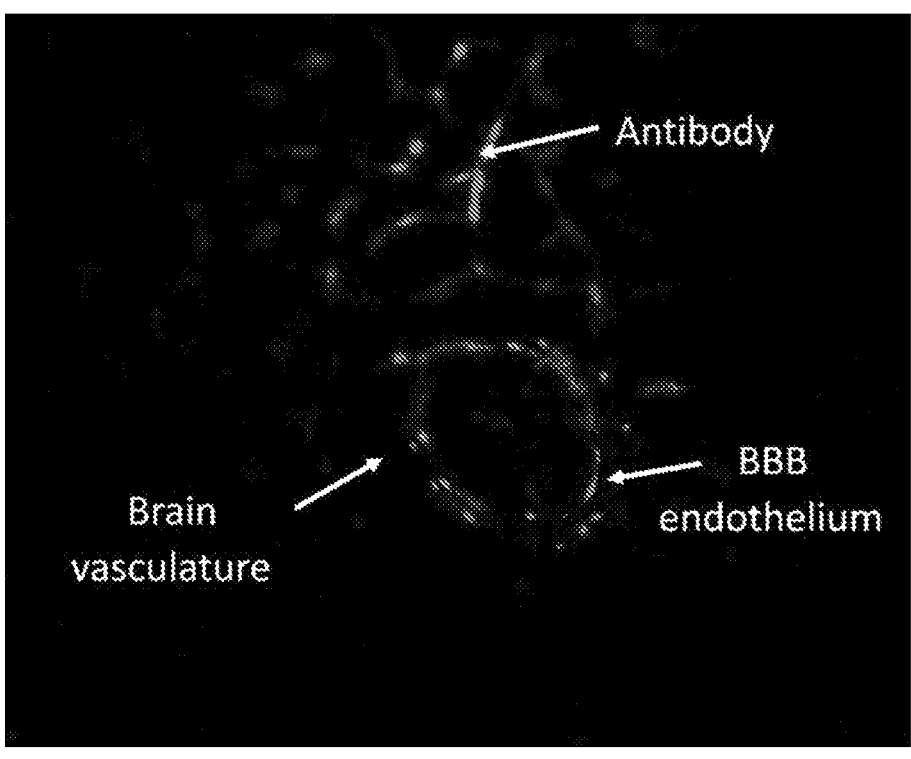
FIGS. 7A-7B: Representative super-resolution microscopy images of frontal brain sections of mice treated with Anti-Iba1 & Ins-GNPs (FIG. 7A) or with free fluorescent anti-Iba1 (FIG. 7B).
Figure 7B:
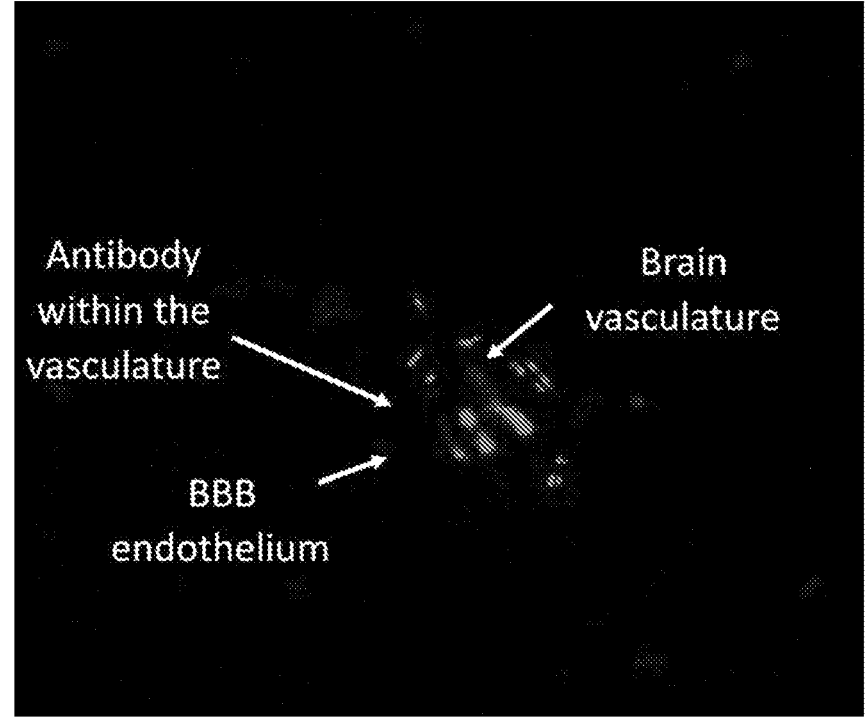

As can be seen in FIGS. 7A and 7B, the super-resolution microscopy images showed the migration of Anti-Iba1 & Ins-GNPs within the brain (7A), while free antibody was blocked within the brain blood vessel (7B).

Example 6: Functionality of Antibody after Covalent Conjugation to the GNP Shuttle In order to make sure that the antibodies remain functional while conjugated to the GNP shuttle, an in vitro experiment was performed with the Anti-TGF-β Antibody fresolimumab. Upon binding of fresolimumab to the TGF-β cytokine secreted by cancer cells, the activity of the immune system is enhanced, as expressed by the elevation of tumor necrosis factor (TNF)-a.

Fresolimumab & Ins-GNPs were synthesized as described in Example 1, with fresolimumab instead of EGFR Ab.

1 µM of fresolimumab & Ins-GNPs were added to a co-culture of F4-T cells with Skmel23-cancer cells with soluble TGFβ. After incubation overnight, TNF-α secretion was quantified using Elisa and compared to that of control cells without fresolimumab & Ins-GNPs.

Interestingly, higher concentration of TNF-α was observed for cells treated with the fresolimumab & Ins-GNPs in comparison to the untreated cells, indicating that although being fixed to the GNP complex by covalent conjugation to a PEG linker, the antibody retains its activity.

Example 7: Delivery of a Peptide & Ins-GNPs into the Brain

In order to examine the ability of the nano platform to deliver peptides into the brain, a cyclic peptide (having a structure presented hereinbelow) that targets the amyloid-beta (Aβ) plaques that exist in the brain of Alzheimer's disease patients was used.

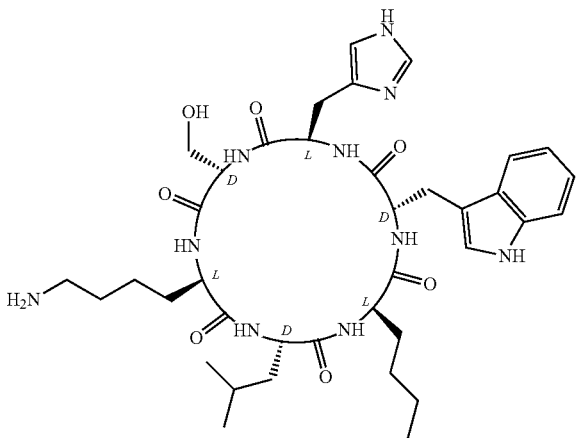

(cyclic D, L-α-peptide; US 2017/0088585)

The cyclic peptide (PEP) was conjugated to Ins-GNPs to form PEP & Ins-GNPs. The synthesis process was performed as described in Example 1, with the cyclic D,L-α-peptide instead of EGFR-Ab.

The particles were characterized following different conjugation steps using UV-vis spectroscopy (FIG. 8), dynamic light scattering (DLS) and zeta potential measurements. Table 1 shows the zeta potential and hydrodynamic diameter of bare GNPs, GNPs+PEG (after first conjugation step) and final particles coated with insulin and peptide.

TABLE 1

Physical characterization of synthesized particles
comprising cyclic peptide as an active agent

| Particle | Size (nm) | Zeta Potential (mV) |
|---|---|---|
| Bare GNP | 23.4 | −38.7 |
| GNP + PEG | 45.1 | −5.95 |
| GNP + PEGs + INS + Peptide | 56.3 | −0.1 |

Figure 8:
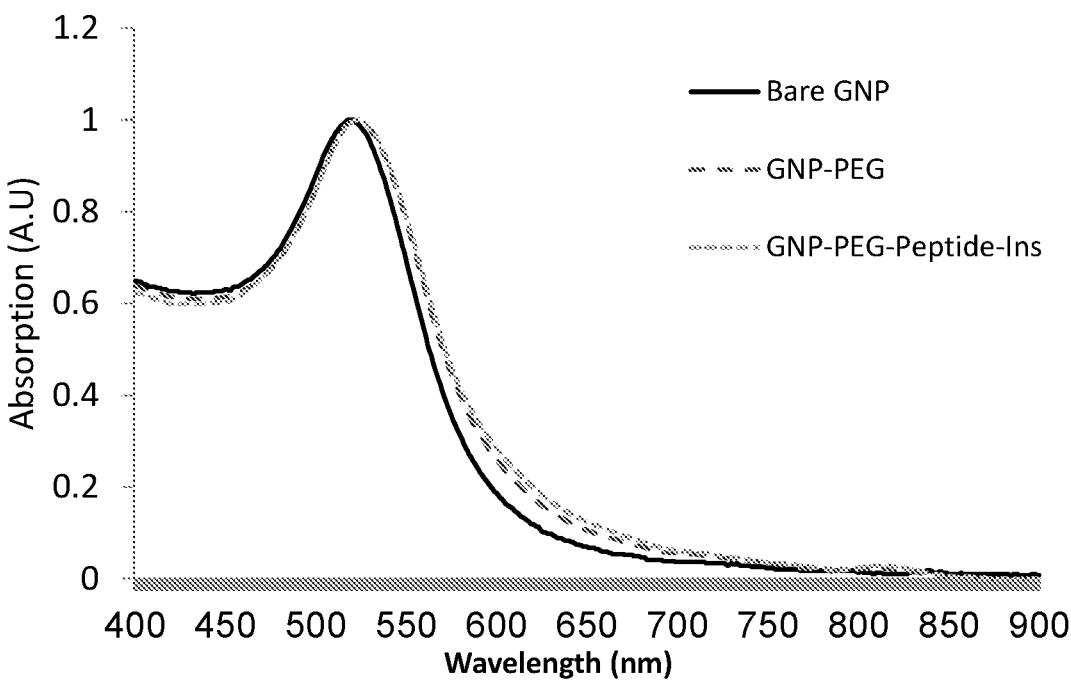
FIG. 8: Ultraviolet-visible spectroscopy of GNPs before coating (bare GNPs); after coating with PEG; and final PEP & Ins-GNPs.

The decrease in zeta-potential value to a nearly neutral level as well as the increase in particle diameter following coating of the particles confirmed the chemical coating. In addition, an expanded and shifted UV-visible signal was observed for the different coating levels (FIG. 8).

For the in vivo experiments, 5×FAD mouse model of Alzheimer's disease (AD, 4 month old) was used.

Figure 9A:
FIG. 9A-9B: Representative Micro-CT images of mice brains 6 hours after intravenous (IV) administration of PEP & Ins-GNPs.
Figure 9B:

PEP & Ins-GNPs were intravenously injected (200 μl, 25 mg/ml) into the tail vein of 5×FAD mice (n=5) and of WT mice (n=5). Six hours Following IV injection, the mice were sacrificed, underwent perfusion and scanned using a micro-CT scanner (FIGS. 9A and 9B). It can be seen that following IV administration, PEP & Ins-GNPs penetrated into the brains of both healthy and diseased mice, with a remarkably higher accumulation in the diseased brain (FIG. 9B) as compared to healthy brain (FIG. 9A).

Figure 9C:
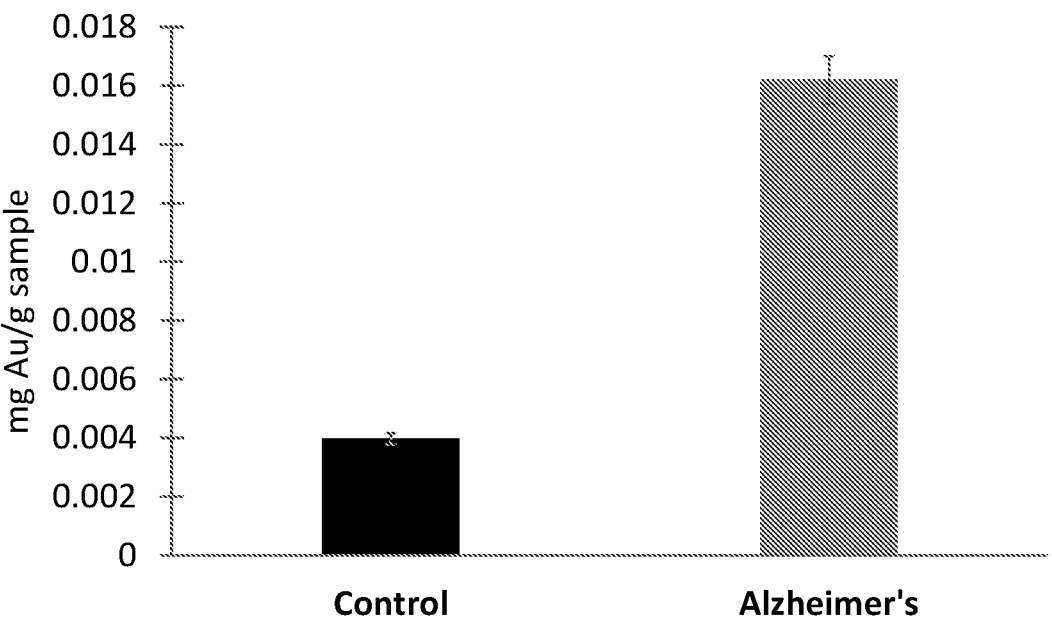
FIG. 9C: Quantification of the amount of Au found in brain tissue of WT mice (control) and 5×FAD mice (Alzheimer's) at 6 hours after intravenous administration of PEP & Ins-GNPs, as measured by ICP-MS analysis (mg Au per gr tissue).

The accumulation of PEP & Ins-GNPs in mice brains was further quantitatively measured by ICP-MS analysis of mice brains' samples (FIG. 9C). The results showed that accumulation of PEP & Ins-GNPs in brains of AD mice was 4 folds higher than in healthy brains, indicating that these particles are gradually cleared from the healthy brain, yet retain in the brain of the AD mice for a longer duration due to the conjugated peptide targeting the Aβ plaques.

Figure 9D:
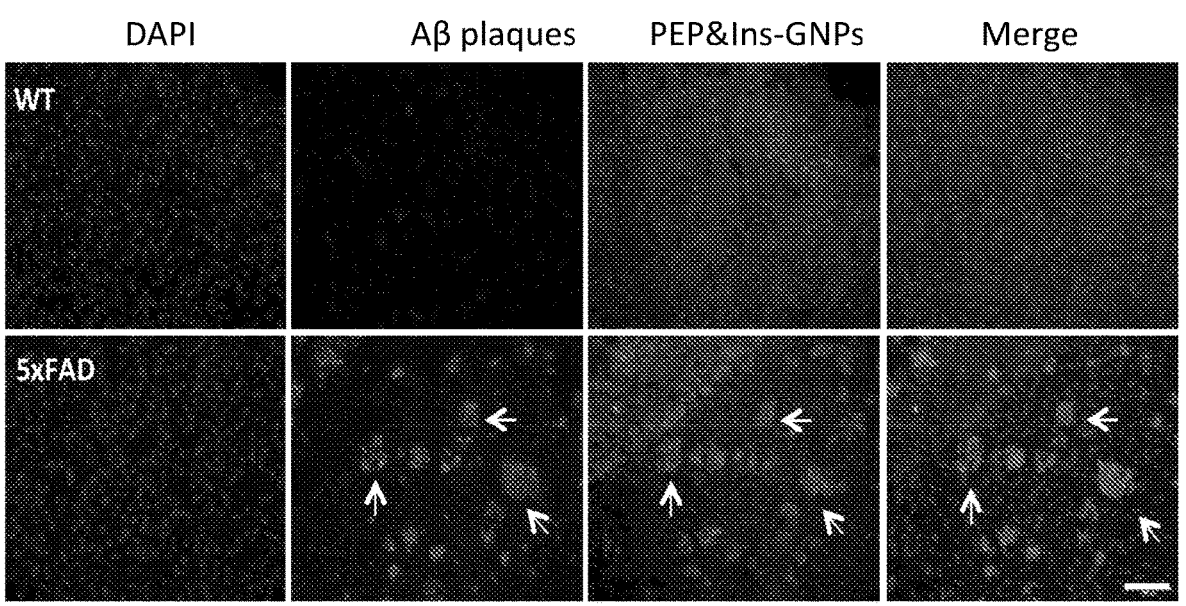
FIG. 9D: Fluorescence microscopy images (×20 magnification; scale bar=100 μm) of hippocampal coronal slices from control mice (WT; top images) or 5×FAD mice (Alzheimer's disease model mice; bottom images) after 20 hours incubation with fluorescently-labeled PEP & Ins-GNPs. Images from left to right: cell kernels localization (DAPI staining); Aβ plaques localization (6E10 staining); PEP & Ins-GNPs localization; and merged fluorescent image.

In order to further examine the targeting abilities of the cyclic peptide, fluorescently-labeled PEP & Ins-GNPs were synthesized, using rhodamine B-labeled peptide. The fluorescently-labeled PEP & Ins-GNPs were incubated for 20 hours at 4° C. with unfixed hippocampal coronal slices from WT or 5×FAD mice. The slices were then co-stained with an anti-Aβ antibody 6E10, to identify Aβ plaques, and DAPI for staining cell kernels. Brain slices from Aβ mice showed distinct staining of PEP & Ins-GNPs, which was co-localized with staining of Aβ plaques (FIG. 9D), indicating that the peptide retains its functionality and targeting capabilities despite being conjugated to the GNP carrier.

Example 8: Delivery of CisPt-Ins-GNPs into Mice Brain

The ability of the GNP platform to deliver a biologically active small molecule into the brain was examined with Cisplatin (CisPt) which is a chemotherapeutic agent with a poor BBB penetration.

Synthesis of Cisplatin+Insulin-GNPs 20 nm spherical GNPs (synthesized as described in Example 1) were first partially coated (80% of particle surface) with mPEG-SH (5 kDa; 60% of particle surface) and a heterofunctional HS-PEG-COOH (1 kDa; 20% of particle surface). Conjugation was performed by adding a mixture of HS-PEG-COOH (39 μl, 50 mg/ml) and mPEG-SH (580 μl, 50 mg/ml) to the GNP solution and mixing for 3 hours. The solution was then centrifuged at 14,000 g for 30 minutes. The precipitate, containing PEG-coated GNPs (80% coating) was transferred to a vial. Cisplatin was then covalently conjugated to the carboxylic group of the HS-PEG-COOH by addition of excess amount of cisplatin with EDC and NHS, followed by mixing for 3 hours at 4° C. Then, the solution was centrifuged at 14,000 g for 30 minutes at 4° C. and the lower phase, containing Cisplatin-GNPs was transferred into a vial.

In order to further conjugate insulin to the GNPs, HS-PEG-COOH (5 kDa) was added (194 μl, 50 mg/ml) to the partially coated GNPs to coat the remaining 20% of particle surface. The solution was then mixed for three hours at 4° C. followed by centrifugation at 14,000 g for 30 minutes at 4° C. Insulin was then covalently conjugated to the free carboxylic groups of the HS-PEG-COOH (5 kDa) by addition of excess amount of insulin together with EDC and NHS. The solution was then stirred for 3 hours at 4° C. followed by centrifugation until a final concentration of 25 mg/ml Au was reached.

In Vivo Experiment

Male BALB/c mice aged 6-7 weeks were administered intravenously through the tail vein with 200 μl of cisplatin+insulin-GNPs (approximately 0.1 mg of cisplatin according to ICP-MS measurement of Pt concentration) (n=3), or with equivalent dose of free Cisplatin (100 μl, 1 mg/ml) (n=3). Mice were sacrificed 8 hours post-administration. The mice underwent perfusion using 20 ml saline to remove all the particles residing within the blood vessels.

After sacrifice and perfusion, mice brains were extracted and weighted followed by ICP-MS analysis to quantify the amounts of Au and Pt within the brain.

Figure 10A:
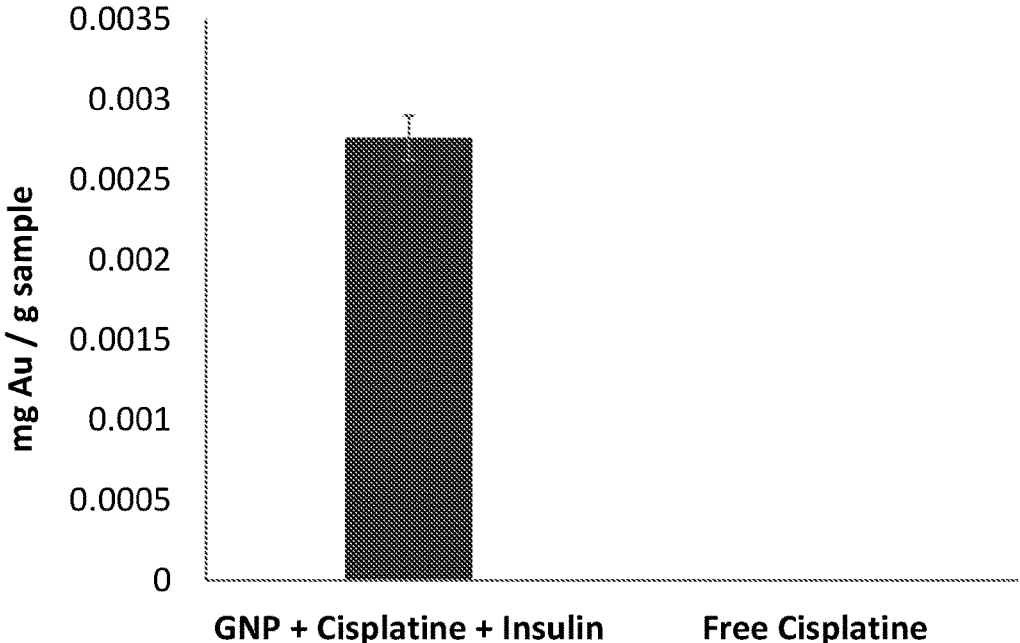
FIG. 10A: Quantification of the amount of Au found in brain tissue of mice 8 hours after intravenous administration of cisplatin+insulin-GNPs or free cisplatin, as measured by ICP-MS analysis (mg Au per gr tissue).
Figure 10B:
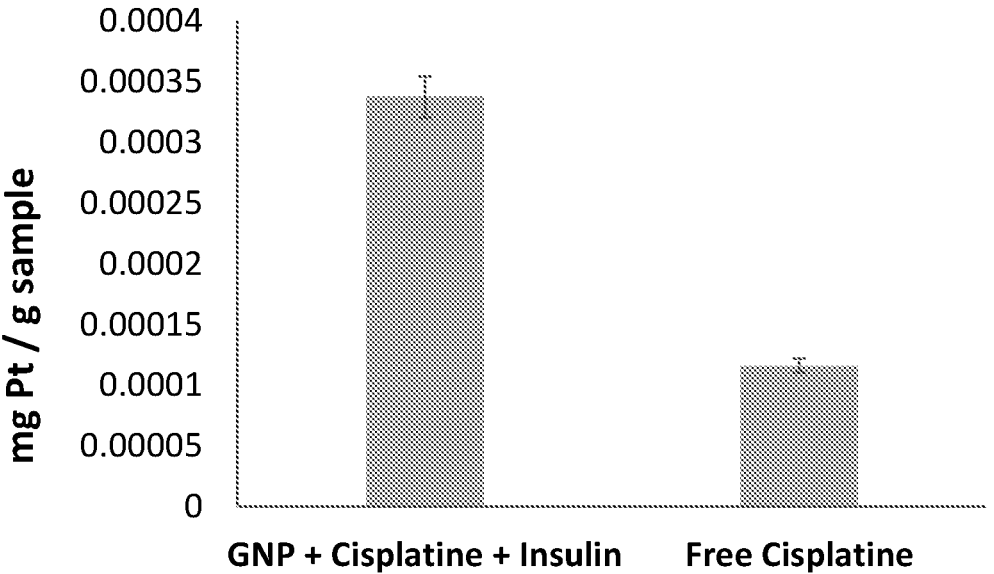
FIG. 10B: Quantification of the amount of Pt found in brain tissue of mice 8 hours after intravenous administration of cisplatin+insulin-GNPs or free cisplatin, as measured by ICP-MS analysis (mg Pt per gr tissue).

As can be seen in FIGS. 10A and 10B, both gold and platin were found within the brains of mice that were administered with cisplatin+insulin-GNPs, indicating successful delivery of the GNPs to the brain. Furthermore, FIG. 10B shows that the amount of Pt found within the brain of mice administered with cisplatin+insulin-GNPs was significantly higher than that after administration of equivalent dose of free cisplatin, indicating that the GNP platform enhances the penetration of the small molecule cisplatin through the BBB.

Additional experiments have been performed with similar GNPs, coated with insulin and with PJ34 as a small molecule drug instead of cisplatin (PJ34-Ins-GNPs). Ex-vivo micro-CT scans of mice brains 24 hours post intravenous administration of these particles showed efficient penetration of PJ34-Ins-GNPs to the brain, providing further evidence for the possibility to deliver small molecule therapeutic agents to the brain using the GNP platform.

Example 9: Delivery of IgG1 & Ins-Coated Iron Oxide Nanoparticles into Mice Brain 50 nm spherical iron-oxide nanoparticles IONPs coated with dextran were purchased from Chemicell. The dextran coating was first removed from the particles by adding double distilled water (DDW) and centrifugation at 12,000 RPM for 30 min.

The IONPs were then coated with insulin and IgG1 antibody through HS-PEG-COOH (~5 kDa) and HS-PEG-COOH (~3.5 kDa), respectively.

The IONPs were first partially coated (85% of particle surface) with mPEG-SH (~5 kDa; 70% of particle surface) and a heterofunctional HS-PEG-COOH (~5 kDa; 15% of particle surface). The amount of mPEG-SH and HS-PEG-COOH required for the partial coating was derived from theoretical calculations based on particle diameter and surface area). Conjugation was performed by adding a mixture of HS-PEG-COOH (58 μl, 50 mg/ml) and mPEG-SH (271 μl, 50 mg/ml) to the IONP solution and mixing for two hours. The solution was then centrifuged and the precipitate, containing PEG-coated IONPs (total 85% coating) was transferred to a vial. Insulin was then covalently conjugated to the carboxylic group of the HS-PEG-COOH by addition of excess amount of insulin on ice together with EDC and NHS followed by mixing for two hours. Then, the solution was centrifuged and the lower phase containing the Ins-PEG-IONPs was transferred into a vial.

For the next coating step, HS-PEG-COOH (~3.5 kDa) was added (41 μl, 50 mg/ml) to the partially coated IONPs to coat the remaining 15% of particle surface. The solution was then mixed for two hours at 4° C. followed by centrifugation. IgG1 was then covalently conjugated to the free carboxylic groups of the HS-PEG-COOH (~3.5 kDa) by addition of excess amount of IgG1 together with EDC and NHS. The solution was then stirred for 2 hours at 4° C. followed by centrifugation until a final concentration of 25 mg/ml Fe was reached.

In Vivo Experiment

Male BALB/c mice (n=3) were intravenously injected with IgG1 & Ins-IONPs (200 μl; 25 mg/ml). After 8 hours, mice were sacrificed and underwent perfusion to remove particles residing within the blood vessels. Then, mice brains were extracted and particles accumulation was evaluated by quantitative measurements of Fe concentration using ICP-MS analysis.

The results indicated that IgG1 & Ins-IONPs efficiently penetrated into the brain, with an Fe concentration of 0.0047 mg Fe per gr brain tissue, at 8 hours post injection. Thus, it can be concluded that different nanoparticle types, in particular IONPs can be used as the nanoparticulate core of the delivery system.

Example 10: BBB Penetration of GNPs Coated with Antibody (IgG1) and Transferrin as a Brain-Internalizing Moiety GNPs coated with IgG1 and transferrin (IgG1 & Trf-GNPs) were synthesized as described in Example 1, using IgG1 antibody instead of EGFR Ab, and human holo-transferrin instead of insulin.

In order to examine their BBB penetration, an in vitro BBB model was used. GHuman induced pluripotent stem cells (iPSCs) differentiated into BMEC-like cells (iBMECs) provide a robust source for human BBB models. iBMECs display molecular, structural, and functional BBB properties, including transendothelial electrical resistance (TEER), closely resembling human brain vasculature. These model of the BBB, uses 2-dimensional (2D) Transwell inserts (Vatine, Gad D., et al. Cell stem cell 20.6 (2017): 831-843; and Lippmann, Ethan S., et al. Scientific reports 4.1 (2014): 1-10).

Half million cells were cultured in the trans wells and grown until its TEER value reached about 3500 Ω×cm2. The TEER was measured and then IgG1 & Trf-GNPs, IgG1 & Ins-GNPs, or mPEG-GNPs (control particles) were introduced into the upper medium (0.25 mg per 1 million cells; n=2 per group). Two hours later, the TEER values were measured again and the TEER reduction was calculated (compared to the initial value prior to particles addition).

Reduction in TEER value means less resistance and indicates an increased permeability through the tight layer of cells.

Figure 11:
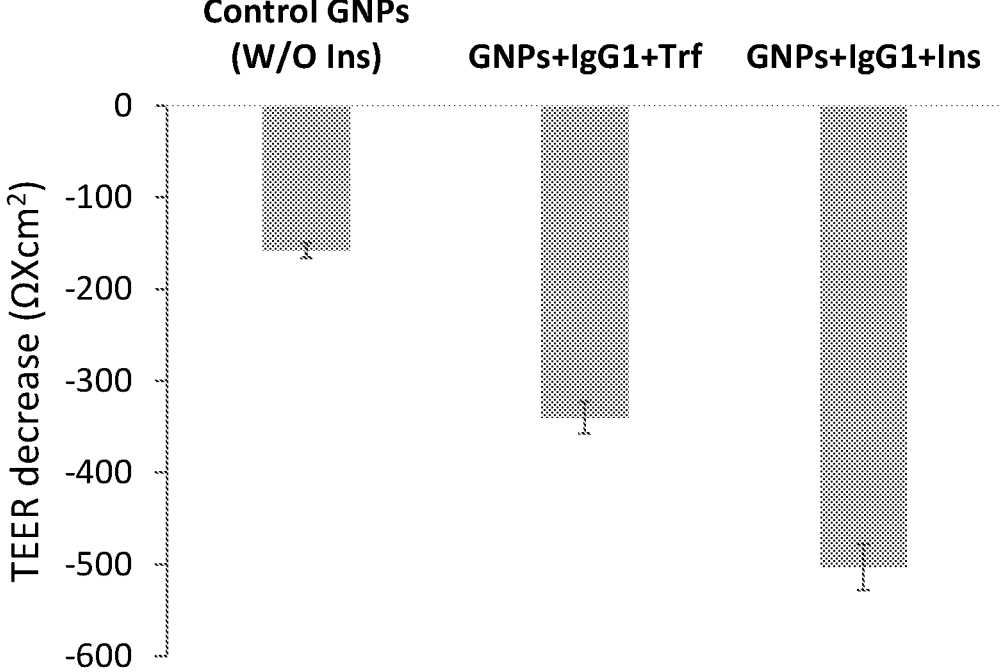
FIG. 11: Transendothelial electrical resistance (TEER) reduction of BMEC-like cells (iBMECs) after 2 hours incubation with mPEG-GNPs (control particles); IgG1 & Trf-GNPs or IgG1 & Ins-GNPs.

FIG. 11 represents the TEER reduction of the three groups. It was found that both IgG1 & Trf-GNPs (GNPs+IgG1+Trf) and IgG1 & Ins-GNPs (GNPs+IgG1+Ins) exhibited an increased permeability through the tight layer of cells as compared to the control GNPs, pointing on the potential of these particles to penetrate into the brain in vivo, due to the conjugated brain internalizing moiety, i.e., insulin or transferrin. However, the insulin-conjugated particles showed a significantly enhanced permeability compared to that of the transferrin-conjugated particles.

Example 11: The Effect of Insulin Levels, Antibody Levels, and Linkers Size on the Ability of the Nano Delivery System to Cross the BBB In order to examine the effect of linkers' size and % coverage of each coating molecule, on the ability of the nano delivery system to cross the BBB, various brain targeted gold nanoparticles coated with insulin and IgG1 Ab were synthesized. Synthesis of all particles was carried out as described in Example 1, except for the MW of the PEG linkers used or their relative amounts (i.e., % coverage). Table 2 specifies the different particles that were prepared and examined.

TABLE 2

| Particles synthesized with different linkers' sizes and relative amounts | |
| --- | --- |
| Particle | PEG layer composition |
| GNP-5% Ins-20% Ab | mPEG-SH ~5 kDa/HS-PEG-COOH ~5 kDa (conjugated to insulin)/HS-PEG-COOH ~3.5 kDa (conjugated to Ab) (mol/mol 75:5:20) |
| GNP-10% Ins-20% Ab | mPEG-SH ~5 kDa/HS-PEG-COOH ~5 kDa (conjugated to insulin)/HS-PEG-COOH ~3.5 kDa (conjugated to Ab) (mol/mol 70:10:20) |
| GNP-15% Ins-20% Ab | mPEG-SH ~5 kDa/HS-PEG-COOH ~5 kDa (conjugated to insulin)/HS-PEG-COOH ~3.5 kDa (conjugated to Ab) (mol/mol 65:15:20) |
| GNP-20% Ins-20% Ab | mPEG-SH ~5 kDa/HS-PEG-COOH ~5 kDa (conjugated to insulin)/HS-PEG-COOH ~3.5 kDa (conjugated to Ab) (mol/mol 60:20:20) |
| GNP-50% Ins-20% Ab | mPEG-SH ~5 kDa/HS-PEG-COOH ~5 kDa (conjugated to insulin)/HS-PEG-COOH ~3.5 kDa (conjugated to Ab) (mol/mol 30:50:20) |
| GNP-20% Ins-40% Ab | mPEG-SH ~5 kDa/HS-PEG-COOH ~5 kDa (conjugated to insulin)/HS-PEG-COOH ~3.5 kDa (conjugated to Ab) (mol/mol 40:20:40) |
| GNP-15% Ins-85% Ab | HS-PEG-COOH ~5 kDa (conjugated to insulin)/HS-PEG-COOH ~3.5 kDa (conjugated to Ab) (mol/mol 15:85) |
| Ins-PEG7- Ab-PEG7 | mPEG-SH ~1 kDa/HS-PEG-COOH 458 Da (conjugated to insulin)/HS-PEG-COOH 458 Da (conjugated to Ab) (mol/mol 60:20:20) |
| Ins-PEG1000- Ab-PEG1000 | mPEG-SH ~1 kDa/HS-PEG-COOH ~1 kDa (conjugated to insulin)/HS-PEG-COOH ~1 kDa (conjugated to Ab) (mol/mol 60:20:20) |
| Ins-PEG3500- Ab-PEG3500 | mPEG-SH ~3.5 kDa/HS-PEG-COOH ~3.5 kDa (conjugated to insulin)/HS-PEG-COOH ~3.5 kDa (conjugated to Ab) (mol/mol 60:20:20) |

TABLE 2-continued

| Particle | PEG layer composition |
|---|---|
| Ins-PEG5000-Ab-PEG3500 (identical to GNP-20% Ins-20% Ab) | mPEG-SH ~5 kDA/HS-PEG-COOH ~5 kDa (conjugated to insulin)/HS-PEG-COOH ~3.5 kDa (conjugated to Ab) (mol/mol 60:20:20) |
| Ins-PEG1000-Ab-PEG3500 | mPEG-SH ~3.5 kDA/HS-PEG-COOH ~1 kDa (conjugated to insulin)/HS-PEG-COOH ~3.5 kDa (conjugated to Ab) (mol/mol 60:20:20) |
| Ins-PEG1000-Ab-PEG5000 | mPEG-SH ~5 kDA/HS-PEG-COOH ~1 kDa (conjugated to insulin)/HS-PEG-COOH ~5 kDa (conjugated to Ab) (mol/mol 60:20:20) |

*Particles synthesized with different linkers' sizes and relative amounts*

The brain-targeted particles listed in Table 1 were intravenously injected (200 μl of 30 mg/ml) into the tail vein of male Balb/C mice (n=2 per group). 8 hrs post injection, mice were sacrificed and underwent perfusion. Then, the brains were extracted and analyzed by ICP-MS to quantify the amount of gold that penetrated through the BBB.

Figure 12A:
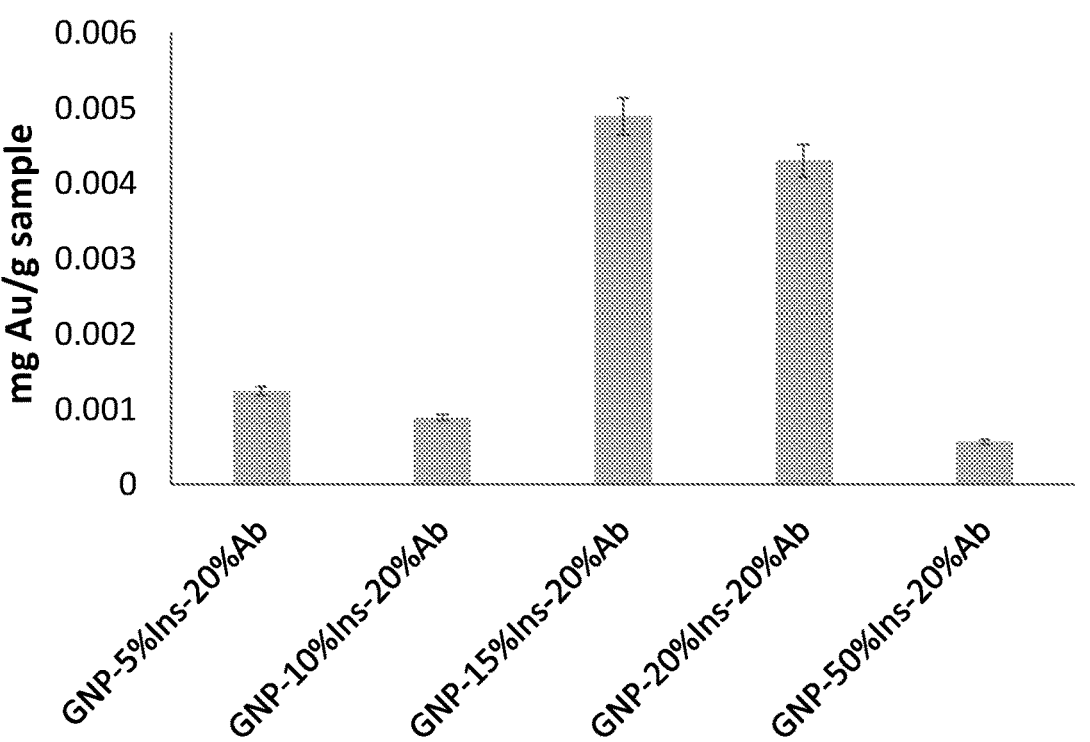
FIG. 12A: Quantification of the amount of Au (mg per gr tissue) found in brains of mice at 8 hours after intravenous administration of IgG1 & Ins-GNPs having different insulin levels, ranging between 5% to 50%.

FIG. 12A demonstrates the effect of insulin levels on the ability of the particle to penetrate into the brain. It can be seen that coating the GNP with insulin at 5% or 10% coverage was not sufficient for delivering significant amount of the administered particles into the brain. However, coating the particle with insulin at 15% or 20% coverage has led to a remarkable brain penetration. Surprisingly, GNPs coated with higher concentration of insulin, i.e., 50%, exhibited a significantly lower penetration into the brain. It is hypothesized that this result can be attributed to steric interference and structural constraints.

Figure 12B:
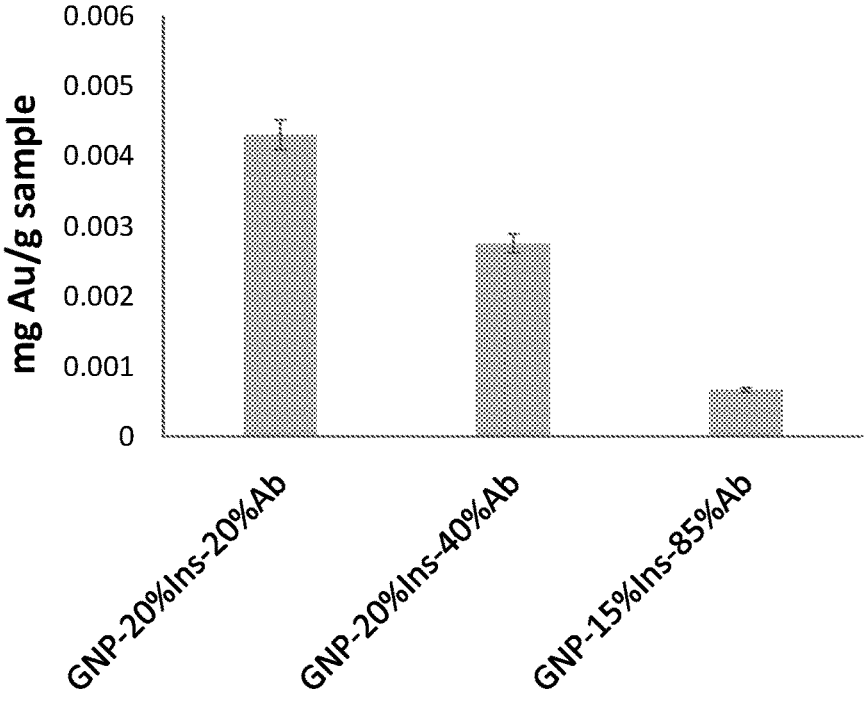
FIG. 12B: Quantification of the amount of Au (mg per gr tissue) found in brains of mice at 8 hours after intravenous administration of IgG1 & Ins-GNPs having different IgG1 Ab levels, ranging between 20% to 85%.

FIG. 12B demonstrates the effect of antibody levels within the nano-delivery system on its ability to penetrate into the brain. It can be seen that among the particles with different antibody levels, GNPs with 20% antibody coating showed the highest brain penetration, while particles with higher antibody levels exhibited lower brain penetration. However, it should be noted that although 40% antibody coating has led to a lower penetration of GNPs as compared to 20% antibody coating, the total amount of antibody penetrated into the brain using these particles is higher due to the higher antibody concentration per particle.

Figure 12C:
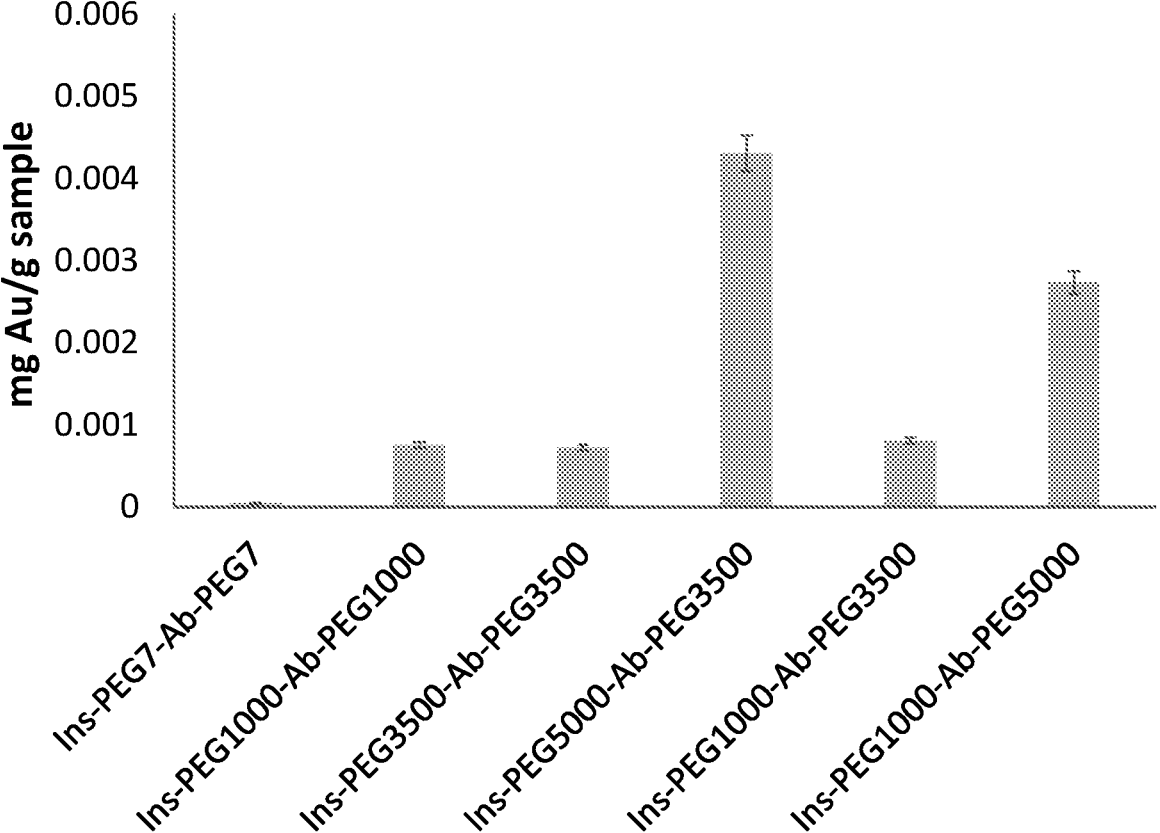
FIG. 12C: Quantification of the amount of Au (mg per gr tissue) found in brains of mice at 8 hours after intravenous administration of IgG1 & Ins-GNPs that were prepared using different sizes of PEG linkers.

FIG. 12C demonstrates the effect of linkers' length on the ability of the particle to penetrate into the brain. It can be seen that the highest brain penetration was obtained using PEG5000 and PEG3500 for insulin and Ab conjugation, respectively. Interestingly, when linkers having a similar size were used for insulin and Ab conjugation (including relatively low MW- and high MW-linkers, namely, MW=458 Da, 1000 kDa and 3500 kDa PEG linkers), a low brain penetration was obtained. Likewise, low brain penetration was obtained when PEG1000 and PEG3500 were used for insulin and Ab conjugation, respectively. These results suggest that in order to achieve an efficient penetration through the BBB into the brain, the insulin which acts as the brain internalizing moiety should be exposed on the surface of the entire nano-delivery system (i.e., to be present on the external surface of the particle shell). Since insulin is significantly smaller than the antibody (5 kDa compared to 150 kDa), in order to remain exposed on the nano-delivery system surface and not to be shielded by the antibody, it has to be conjugated to a linker, which is longer than the linker used to bound the antibody.

Interestingly, when the antibody and insulin were conjugated to a 5 kDa PEG linker and 1 kDa PEG linker, respectively, significant brain penetration was obtained (which was however lower than that obtained with Ins-PEG5000-Ab-PEG3500). Without wishing to being bound by theory or mechanism of action, this result may be explained by potential folding of the 5 kDa PEG linker, such that its actual length (i.e., end-to-end distance) is shorter, thereby enabling exposure of the insulin moiety.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A nano-delivery system comprising:
(a) an inorganic nanoparticle bound to a first linear polymeric linker and to a second linear polymeric linker, wherein the first linear polymeric linker has a substantially increased molecular weight of at least 1000 Da or a substantially increased end-to-end displacement length when compared to the second linear polymeric linker;
(b) a brain internalizing transporter moiety conjugated to the first linear polymeric linker through a first functional end group of the first linear polymeric linker; and
(c) an active agent selected from a biologically active molecule or a labeling molecule, wherein the active agent is conjugated to the second linear polymeric linker through a second functional end group of the second linear polymeric linker;
wherein the molecular weight of the first and the second linear polymeric linkers is within the range of 1,000-10,000 Da.

2. The nano-delivery system according to claim 1, wherein the first and the second polymeric linkers are non-cleavable under physiological conditions.

3. The nano-delivery system according to claim 1, wherein the inorganic nanoparticle is bound to the second linear polymeric linker through a sulfide bond and the active agent is conjugated to the second linear polymeric linker through an amide bond.

4. The nano-delivery system according to claim 1, wherein the first and the second linear polymeric linkers are each constitutes from about 5% mol to 60% mol of the total polymeric linkers bound to the inorganic nanoparticle.

5. The nano-delivery system according to claim 1, wherein the active agent is a biologically active molecule selected from the group consisting of a macromolecule, an antibody, a peptide, a small molecule, an oligonucleotide, an antisense RNA, and any combination thereof.

6. The nano-delivery system according to claim 1, wherein the first linear polymeric linker and the second linear polymeric linker independently comprise a polymer selected from the group consisting of: a polyether, a polyacrylate, a polyanhydride, a polyvinyl alcohol, a polysaccharide, a poly(N-vinylpyrrolidone), a polyglycerol (PG), a poly(N-(2-hydroxypropyl) methacrylamide), a polyoxazoline, a poly (amino acid)-based hybrid, a recombinant polypeptide, derivatives, and combinations thereof.

7. The nano-delivery system according to claim 6, wherein at least one of the first linear polymeric linker and the second linear polymeric linker is a polyether, wherein the polyether is polyethylene glycol (PEG), and wherein the polyethylene glycol (PEG) is selected from a thiolated PEG acid (HS-PEG-COOH) and a thiolated PEG amine (HS-PEG-NH2).

8. The nano-delivery system according to claim 1, further comprising a third polymeric linker bound to the inorganic nanoparticle, wherein the third polymeric linker is monofunctional.

9. The nano-delivery system according to claim 8, wherein the third polymeric linker comprises a polymer selected from the group consisting of a polyether, a methoxy polyethylene glycol (mPEG), a polyacrylate, a polyanhydride, a polyvinyl alcohol, a polysaccharide, a poly(N-vinylpyrrolidone), a polyglycerol (PG), a poly(N-(2-hydroxypropyl) methacrylamide), a polyoxazoline, a poly (amino acid)-based hybrid, a recombinant polypeptide, derivatives, and combinations thereof.

10. The nano-delivery system according to claim 1, wherein the inorganic nanoparticle is selected from the group consisting of a metal nanoparticle, a metal oxide nanoparticle, a ceramic nanoparticle, and any combination thereof.

11. The nano-delivery system according to claim 10, wherein the metal nanoparticle is selected from the group consisting of gold, silver, platinum, iron, and any combination thereof and/or wherein the metal oxide nanoparticle is selected from the group consisting of iron oxide, iron (III) oxide, iron (II,III) oxide, magnesium oxide, nickel oxide, cobalt oxide, aluminum oxide, zinc oxide, copper oxide, manganese oxide, and any combination thereof.

12. The nano-delivery system according to claim 1, wherein the brain-internalizing transporter moiety is selected from the group consisting of: insulin, an antibody specific for the insulin receptor, transferrin, an antibody specific for the transferrin receptor, a polypeptide that specifically binds to the transferrin receptor, a polypeptide that specifically binds to the insulin receptor, insulin-like growth factor 1, an antibody specific for the insulin-like growth factor receptor 1, a polypeptide that specifically binds to the insulin-like growth factor receptor 1, apolipoprotein A1, B, or E, lactoferrin, angiopep-2, a low-density lipoprotein, an antibody specific for low density lipoprotein receptor or lipoprotein receptor-related protein, a polypeptide that specifically binds to low density lipoprotein receptor or lipoprotein receptor-related protein, an antibody specific for diphtheria toxin receptor, a polypeptide that specifically binds to diphtheria toxin receptor, a BBB-penetrant cell-penetrating peptide (CPP), and any combination thereof.

13. The nano-delivery system according to claim 12, wherein the brain-internalizing transporter moiety is insulin.

14. The nano-delivery system according to claim 1, wherein the inorganic nanoparticle has a diameter of 10-160 nm.

15. A pharmaceutical and/or diagnostic composition comprising the nano-delivery system of claim 1 and a pharmaceutically acceptable carrier.

16. The pharmaceutical composition of claim 15, wherein the pharmaceutical and/or diagnostic composition is formulated for at least one of an intravenous (IV) administration, an intranasal (IN) administration and intrathecal (IT) administration.

* * * * *